(12) United States Patent
Hala et al.

(10) Patent No.: US 6,507,804 B1
(45) Date of Patent: Jan. 14, 2003

(54) APPARATUS AND METHOD FOR COMPRESSING MEASUREMENT DATA CORELATIVE TO MACHINE STATUS

(75) Inventors: Roger A. Hala; Michael Alan Tart, both of Gardnerville; Joseph D. Miguel, Carson City, all of NV (US)

(73) Assignee: Bently Nevada Corporation, Minden, NV (US)

( * ) Notice: Subject to any disclaimer, the term of this patent is extended or adjusted under 35 U.S.C. 154(b) by 0 days.

(21) Appl. No.: 09/503,644

(22) Filed: Feb. 14, 2000

Related U.S. Application Data

(63) Continuation-in-part of application No. 08/949,905, filed on Oct. 14, 1997, now Pat. No. 6,026,348.

(51) Int. Cl.[7] ............................................. G01M 13/00

(52) U.S. Cl. ........................ 702/182; 702/189; 702/183; 702/56; 73/660

(58) Field of Search ...................... 702/182, 56, 33–35, 702/38, 41–44, 54, 70–72, 76, 77, 79, 103–106, 188, 124, 113–115, 126, 141, 180, 183–187, 189–191, 193–195, 198, 145–148, FOR 123–FOR 126, FOR 135, FOR 136, FOR 168, FOR 171; 324/76.13, 76.15, 76.22, 76.33; 340/683, 870.16, 679, 680; 73/583, 579, 116, 659, 660, 570, 577, 578, 66, 582, 618, 457, 462, 1.14, 778, DIG. 1; 704/205, 500, 501, 503, 504, 201, 203, 224, 228; 700/73, 74, 275, 280, 279, 174, 175, 177; 708/203, 403

(56) References Cited

U.S. PATENT DOCUMENTS

| | | | |
|---|---|---|---|
| 2,763,840 A | 9/1956 | Pfleger | 333/17.1 |
| 3,462,555 A | 8/1969 | Presti | 704/205 |
| 3,471,648 A | 10/1969 | Miller | 704/224 |
| 3,620,069 A | 11/1971 | Cole, Jr. | 73/583 |
| 3,641,550 A | 2/1972 | Lynas et al. | 73/583 |
| 3,681,530 A | 8/1972 | Manley et al. | 704/203 |
| 3,742,395 A | 6/1973 | Yoneyama | 333/17.1 |
| 3,758,758 A | 9/1973 | Games et al. | 702/56 |
| 3,936,611 A | 2/1976 | Poole | 704/503 |
| 3,959,592 A | 5/1976 | Ehrat | 380/28 |
| 4,081,749 A | 3/1978 | Peterson | 370/292 |
| 4,157,457 A | 6/1979 | Sakoe et al. | 704/205 |
| 4,408,285 A | 10/1983 | Sisson et al. | 702/56 |
| RE31,750 E | 11/1984 | Morrow | 702/34 |
| 4,480,480 A | 11/1984 | Scott et al. | 73/769 |
| 4,488,240 A | 12/1984 | Kapadia et al. | 702/56 |
| 4,553,213 A | 11/1985 | Hyatt | 332/185 |
| 4,590,466 A | 5/1986 | Wiklund et al. | 340/870.28 |
| 4,621,263 A | 11/1986 | Takenaka et al. | 340/890.07 |
| 4,908,785 A | 3/1990 | Cubbins et al. | 702/190 |
| 4,912,661 A | 3/1990 | Potter | 702/147 |
| 5,115,671 A | 5/1992 | Hicho | 73/488 |

(List continued on next page.)

FOREIGN PATENT DOCUMENTS

WO    WO99/19698    4/1999

Primary Examiner—Hal Wachsman
(74) Attorney, Agent, or Firm—Dennis DeBoo

(57) ABSTRACT

A method and apparatus for compressing, storing and transmitting measurement data correlative to machine status is disclosed in which the measurement data is continuously sensed, sampled and processed to extract significant spectral elements including magnitude and phase information from each successive period of the originally measured data and to store those spectral elements in a memory means from an initial period of significant spectral elements and each successive period of significant spectral elements which have changed since the previous period for developing a compressed data history correlative to a continuous history of the status of the machine being monitored and from which continuous signals can be regenerated and analyzed for any earlier historical time.

10 Claims, 29 Drawing Sheets

U.S. PATENT DOCUMENTS

| | | | |
|---|---|---|---|
| 5,303,346 A | | 4/1994 | Fesseler et al. ............. 704/230 |
| 5,309,149 A | | 5/1994 | Bozeman, Jr. ............... 340/683 |
| 5,311,561 A | | 5/1994 | Akagiri ...................... 375/240 |
| 5,365,787 A | | 11/1994 | Hernandez et al. ........... 73/660 |
| 5,394,349 A | | 2/1995 | Eddy .......................... 708/401 |
| 5,407,265 A | * | 4/1995 | Hamidieh et al. .......... 700/175 |
| 5,426,665 A | | 6/1995 | Cleverly et al. ............ 375/150 |
| 5,430,241 A | | 7/1995 | Furuhashi et al. ............ 84/603 |
| 5,453,945 A | | 9/1995 | Tucker et al. ............... 708/400 |
| 5,485,160 A | | 1/1996 | Suganuma .................. 342/195 |
| 5,502,650 A | | 3/1996 | Naruse et al. ............... 700/279 |
| 5,519,166 A | | 5/1996 | Furuhashi et al. ............ 84/603 |
| 5,519,645 A | | 5/1996 | Bohley ........................ 702/76 |
| 5,544,073 A | | 8/1996 | Piety et al. .................. 700/279 |
| 5,602,749 A | | 2/1997 | Vosburgh .................... 700/174 |
| 5,852,793 A | | 12/1998 | Board et al. ................... 702/56 |
| 5,895,857 A | * | 4/1999 | Robinson et al. ............. 73/660 |
| 5,922,963 A | * | 7/1999 | Piety et al. ................... 73/660 |
| 6,026,418 A | * | 2/2000 | Duncan, Jr. .................. 702/77 |

\* cited by examiner

APPARATUS AND METHOD FOR COMPRESSING MEASUREMENT DATA CORELATIVE TO MACHINE STATUS

CROSS REFERENCE TO RELATED APPLICATION

This is a continuation in part of application Ser. No. 08/949,905, filed Oct. 14, 1997 patented Feb. 15, 2000, as U.S. Pat. No. 6,026,348. The disclosure of which is hereby incorporated by reference.

FIELD OF THE INVENTION

The present invention relates generally to a method and apparatus for compressing measurement data correlative to machine status, and in particular, to a method and apparatus for compressing machine vibration data to allow significant compression of the original data for storage and transmission wherein the compressed data can be retrieved and reconstructed to provide a complete continuous waveshape history of machine performance.

BACKGROUND OF THE INVENTION

Machinery monitoring systems have been permanently installed in, inter alia, today's large process plants, power generation stations and pipelines in an attempt to provide machinery protection by continuously monitoring the behavior and performance characteristics of machinery at a multiplicity of points and possibly acquiring data from these points simultaneously. More recently, the trend has been to enhance the monitoring systems by directly interfacing computers to the systems for periodically collecting data from these systems for historical trend, machinery diagnostics and predictive maintenance purposes. However, these current systems use methods which only retain a small history of machine performance at best.

For example, current systems periodically collect, store, display and print machinery data in a variety of formats using a variety of schemes. One such scheme is to continuously sample and store data at a high sample rate to obtain data with relatively high data time resolution, and as storage space fills, to replace the stored data with a new data set. This scheme does not automatically store the historical information necessary to analyze one or more problems, may not represent a long enough period of time to represent the on-set of one or more problems and does not readily identify the occurrence of one or more problems.

Another scheme is to intermittently capture data "snapshots" of the machine performance. A small set of "snapshots" are maintained in memory and saved in the event of a machine problem. However, the time represented by the "snapshots" may not be adequate to represent historical machine performance or may not represent a continuous set of data with the machine fault occurring between data sets previously stored in memory.

A common scheme is to represent the machine performance with an overall magnitude, eliminating all of the details that are contained to generate the magnitude. Although the magnitude can be used for protection, it does little to identify the causes of the problem.

The disadvantage of these schemes is they either consume too much memory, may not provide a rapid method to identify when one or more problems commence and to describe its progress or may lose the ability to diagnose one or more problems after the fact by either destroying the data with replacement information, or by taking data samples with the data of interest falling between the samples.

Therefore, if one were to continuously capture the machine data using current techniques, the memory requirements of such data storage can be enormous considering that the data is preferably collected over a period of months or years. In addition, long transmission times are required for transmitting large quantities of continuous machine data to a remote data base for permanent storage and with enough detail and history to perform fault analysis and diagnosis.

In addition, with current systems it is a challenge to capture and store infrequently occurring machine anomalies and to ensure that these anomalous events get managed using past learning experiences and procedures according to historical data. For example, the cause of and the procedures needed to deal with these machine anomalies may not be repetitive enough to stay within peoples' memory. Further, to make matters worse, many anomalous events occur so infrequently that people who managed and learned from previous situations have either changed jobs or are not available by the time a similar anomalous event occurs again. These anomalous events can have a profound impact if not managed correctly. For example, improper management of one of these anomalous events may cause loss of life, loss of property, fugitive emissions and other undesirable consequences.

Therefore, what is needed is a system which, inter alia, allows machine data to be compressed and stored in a reduced form which represents a continuous set of data correlative to a continuous history of machine performance without allowing machine faults between data sets to go undetected and thus unrepresentable. In addition, a need exists for a system which reduces data volume sufficiently to allow transmission using commonly available transmission media. Furthermore, a need exists for a system which allows stored compressed data to be retrieved and reconstructed to provide a complete continuous waveshape history of machine performance. Moreover, a system is needed which provides continuous data acquisition for diagnostic and predictive maintenance purposes for maximizing the machine's life while minimizing its cost and averting any catastrophic events when in operation.

U.S. Pat. No. 4,908,785 issued Mar. 13, 1990, to Cubbins, et al., teaches the use of a data compression method for telemetry of vibration data. The method achieves compression by filtering the incoming signal to extract a low frequency band. This low frequency band is sent to a multiplexed system without encryption or compression but can be sampled at a lower frequency since the upper frequency has been significantly reduced. The total range of frequencies is then divided, either by fractional octave filters, DFT or FFT to amplitude detect bands of frequencies and then the magnitude of the signals in this band or bands are extracted. These magnitudes are multiplexed with the lower frequency signals to give an overall or specific distribution of energy. Once processed, the low frequency data can be extracted but a waveshape can not be generated from the information present.

SUMMARY OF THE INVENTION

The present invention is distinguished over the known prior art in a multiplicity of ways. For one thing, the present invention provides a system for compressing, storing and transmitting raw dynamic machine data in a reduced form which can be retrieved and reconstructed into a continuous set of data correlative to a continuous waveshape history of machine performance without allowing machine faults between data sets to go undetected and thus unrepresentable.

In addition, the present invention reduces data volume sufficiently to allow transmission using commonly available transmission media by, inter alia, retaining only significant data and by eliminating data created from noise sources. Furthermore, the present invention provides a system which continuously collects and stores information on machine performance to generate a historical data base which captures, inter alia, infrequently occurring machine anomalies and allows historical dynamic machine performance data to be retrieved and reconstructed including machine phase information. The system also allows a rule set to be generated from the historical data which is an accurate assessment of these anomalous events. The present invention further provides a system which allows access to the data base at any time so that past learned machine performance can be used. Moreover, the present invention provides a system which, inter alia, provides continuous life time data acquisition for diagnostic and predictive maintenance purposes for maximizing the machines life while minimizing its cost and averting any catastrophic events when in operation.

In one preferred form, the system of the present invention includes a computational means operatively coupled to a sampling means and to at least one machine, for example, to at least one bearing or measurement point to be monitored. The system is adapted to receive signals from a plurality of sensors operatively coupled to the machine. Preferably, the sampling means is operatively coupled to and receives data from at least one sensor sensing raw dynamic machine vibration signals correlative to machine status. Preferably, the computational means incorporates a timing pulse into commands given to the sampling means for synchronously sampling the raw dynamic machine vibration signals into discrete digital values. Alternatively, the computational means can issue commands to the sampling means for sampling the raw dynamic machine vibration signals into discrete digital values asynchronously with machine speed. These discrete digital values are transmitted to the computational means and are processed in sets according to the present invention.

The computational means performs a fast fourier transform analysis on a first data set of digital values to preferably transform the data into a series of spectral elements including both amplitude and phase information. The spectral elements are compared to a dominate criteria and those which pass this criteria are stored in a memory means along with a unique identifying tag. The identifying tag preferably tags each spectral element with an element number and a real time value identifying a time in history when the corresponding instantaneous value of the raw vibration signal was captured from the vibration sensor. The spectral elements of the first data set which have passed the dominate criteria can be transmitted to and stored in, for example, the host computer along with at least one unique identifying tag associating an element number and real-time value to each transmitted spectral element.

The computational means transforms a subsequent set of digital values into a subsequent series of spectral elements which are compared to the dominate criteria and those which pass are stored in the memory means and compared to the first set of spectral elements which have been previously stored in the memory means for determining any anomalous behavior between the two. Only those elements included in the subsequent series which are anomalous, because they differ by a comparison criteria from the first set of spectral elements are stored in the memory means. In addition, the anomalous spectral elements in the subsequent series can be transmitted to and stored in the host computer along with at least one unique identifying tag associating an element number and a real-time value to each transmitted spectral element.

The computational means transforms each further subsequent set of digital values into further subsequent series of spectral elements which are each compared to the dominate criteria and those which pass are compared to the previous set of spectral elements which have been stored in the memory means for determining any anomalous behavior between subsequent sets. Only those elements included in each further subsequent series which are anomalous are stored in the memory means and can be transmitted to and stored in the host computer along with at least one unique identifying tag associating an element number and a real-time value to each transmitted spectral element. In addition, information regarding the sample rate of the raw vibration signals is stored in the memory means and transmitted to and stored in the host computer.

The data is preferably transmitted to and stored in the host computer as a spectral frequency element number, in phase and quadrature magnitudes and/or amplitude and phase elements and a real time reference. The spectral frequency is preferably related to shaft speed or time. After receipt of the data, the host computer can perform an inverse fourier transform to regenerate a continuous waveshape from the significant spectral content for any given time in history.

For example, the computer can recreate a continuous waveshape at any given time by using the anomalous spectral elements representing performance for that time. These are accessed by sequencing backwards through the stored spectral element sets to identify and use only those elements whose magnitudes are found to have significance at the desired point in time. These elements will have been identified to have a significant magnitude and/or phase prior to the desired point in time and will exist to a time later than the desired point. The combination of all elements which fit this existence criteria will be included to construct the waveshape. Thus, a continuous waveshape history of machine status at any given time may only require a few anomalous spectral elements to be stored for that given time. Therefore, the present invention provides a significant improvement in data compression, the consumption of memory to store this data and the time needed to transmit this data to a remote location.

The compression method of this invention is a lossy technique and thus, once the data is compressed the original signal cannot be recreated exactly. However, the compression technique of the present invention is highly effective because it only retains the significant content of the data and it preferable only stores the data if it has changed from previously stored data.

OBJECTS OF THE INVENTION

An object of the present invention is to provide a new, novel and useful apparatus and method for compressing measurement data correlative to machine status.

A further object of the present invention is to provide an apparatus and method as characterized above which collects measurement data at a predetermined mode and samples the data input over a number of input cycles and transforms the data using a fast fourier transform method.

Another further object of the present invention is to provide an apparatus and method as characterized above for compressing, storing and transmitting raw dynamic machine data in a reduced form.

Another further object of the present invention is to provide an apparatus and method as characterized above which reduces data volume sufficiently to allow transmission using commonly available transmission media by retaining only significant data.

Another further object of the present invention is to provide an apparatus and method as characterized above which reduces data volume by eliminating data created by noise sources in the system.

Another further object of the present invention is to provide an apparatus and method as characterized above which allows historical dynamic machine performance data to be retrieved and reconstructed including machine phase information.

Another further object of the present invention is to provide an apparatus and method as characterized above for providing a continuous set of data correlative to a continuous history of machine performance without allowing machine faults between data sets to go undetected and thus unrepresentable.

Another further object of the present invention is to provide an apparatus and method as characterized above which continuously collects and stores information on machine performance to generate a historical data base which captures, inter alia, infrequently occurring machine anomalies.

Another further object of the present invention is to provide an apparatus and method as characterized above which allows access to the data at any time so that past learned machine performance can be used.

Another further object of the present invention is to provide an apparatus and method as characterized above which provides continuous lifetime data acquisition for diagnostic and predictive maintenance purposes.

Viewed from a first vantage point, it is an object of the present invention to provide a signal processing method for processing machinery signals correlative to machine status, the steps including: sensing signals correlative to machine status; converting said signals into digital values; storing a series of said digital values into packets; comparing a subsequent packet of said digital values with one said stored packet of said digital values; storing only said digital values included in said subsequent packet which are anomalous because they differ by a criteria from comparable digital values of said previously stored packet of said digital values; transmitting a signal correlative to said packet of digital values and to the subsequent packets including flagging anomalous data in said subsequent packets of digital values.

Viewed from a second vantage point, it is an object of the present invention to provide a machine vibration signal processing method, the steps including: sampling a vibration signal; subjecting said vibration signal to a transformation means for transforming said vibration signal into a series of spectral elements; comparing said series of spectral elements against a criteria for retention and storing in a memory means said spectral elements which pass said criteria; sampling a subsequent vibration signal; subjecting said subsequent vibration signal to said transformation means for transforming said subsequent vibration signal into a subsequent series of spectral elements; comparing said subsequent series of spectral elements to said criteria for retention and then comparing said subsequent series of spectral elements which have passed said criteria for retention with said previously stored series of spectral elements; storing in said memory means spectral elements of said subsequent series which have passed said criteria for retention and which differ from said spectral elements of said previous series by a pre-determined amount.

Viewed from a third vantage point, it is an object of the present invention to provide an apparatus for compressing data correlative to continuous machine vibrations signals, comprising, in combination: at least one sensor operatively coupled to a machine for sensing machine vibration in the form of continuous electrical signals; sampling means adapted to receive from said sensor continuous electrical signals and to converting into digital values said electrical signals; a control circuit commanding said sampling means to convert said electrical signals into digital values; means for uniquely tagging each digital value with each command by said control circuit including a real time value for identifying a time in history of when the corresponding instantaneous value of the continuous electrical signal was captured; means for storing in a memory means a periodicity of said digital values; means for comparing at least one said periodicity of said digital values with a subsequent periodicity of said digital values to determine anomalous digital values, and means for storing in said memory means said anomalous digital values of said subsequent periodicity of said digital values which have changed from said previous periodicity of said digital values.

Viewed from a fourth vantage point, it is an object of the present invention to provide a machine vibration signal processing method, the steps including: sampling continuous vibration signals from a machine; transforming said vibration signals into discrete digital values; storing at least one packet of digital values in a memory means and storing a marker in said memory means for identifying the position and the time of capture of each digital value; comparing a subsequent packet of digital values with at least one said packet of digital values; storing digital values of said subsequent packet of digital values which differ from at least one said packet of digital values and storing markers for identifying the position and time of capture of each differing value; comparing further subsequent packets of digital values with previously stored packets of digital values; storing digital values of said further subsequent packets of digital values which differ from said previously stored values and storing markers in said memory means identifying the position and time of capture of each differing value; reconstituting any packet of digital values into a continuous wave form from the values stored for said packet and from the values of previous packets which correspond to the missing values of said packet being reconstituted.

Viewed from a fifth vantage point, it is an object of the present invention to provide a signal compression method for storing historical data correlative to devolving machine status, the steps including: sensing signals correlative to machine status; sampling said signals; transforming said sampled signals into a series of spectral elements defining a first reading; determining dominate spectral components of a periodicity of said series of spectral elements based on a pre-determined criteria; storing said periodicity of dominate spectral components; determining dominate spectral components of a subsequent periodicity of said series of spectral elements based on said pre-determined criteria; comparing said subsequent periodicity of dominant spectral components with said previously stored periodicity of dominant spectral components to ascertain devolvement in respect of spectral components correlative to machine status; transmitting to and storing in a host computer said spectral components of said subsequent periodicity which change from said spectral components of said previously stored spectral components and when the changes occur; defaulting to resensing in the absence of devolvement; generating a continuous signal correlative to a continuous signal in which said subsequent periodicity of dominant spectral components was produced from by transforming said stored components of said subsequent periodicity and said stored components of said previous periodicity which fails to differ from said subsequent periodicity of dominant spectral components.

Viewed from a sixth vantage point, it is an object of the present invention to provide a method for compressing data from waveforms characterizing machine vibration, the steps including: successively producing a series of samples representing generally instantaneous values of a series of waveforms at time-spaced intervals; transforming a first period of said samples of a first waveform included in said series of waveforms into a first series of spectral elements storing only those elements in said first series of spectral elements which are significant based on a predetermined criteria; transforming said series of samples of each subsequent waveform included in said series of waveforms into a subsequent series of spectral elements; successively storing only those elements in each said subsequent series which have changed since the last stored elements in said series of spectral elements.

Viewed from a seventh vantage point, it is an object of the present invention to provide a method for compressing measurement data correlative to machine status, the steps including: sensing machine data correlative to machine status; sampling said data; transforming said sampled data into spectral elements; comparing said spectral elements to a user definable criteria for retention; storing in a memory means those spectral elements which have passed said user definable criteria for retention wherein said stored elements are correlative to machine status.

Viewed from a eighth vantage point, it is an object of the present invention to provide a method for compressing measurement data correlative to machine status, the steps including: continuously sensing cyclic machine vibration from at least one machine in the form of electrical signals correlative to machine status; sensing at least one mechanical phase reference mark on a rotating shaft of at least the one machine; relating the mechanical phase reference mark of the rotating shaft to the electrical signals of machine vibration wherein the mechanical angle defines intervals of electrical signals; sampling the machine vibration electrical signals under the orchestration of a control signal; transforming said sampled signals into spectral elements; converting said spectral elements into amplitude and phase elements; comparing both the magnitude and phase of each subsequent interval of elements with a previous interval of elements to determine if the amplitude and/or phase of each subsequent element has changed more than a user definable amount from the element of a previous interval; communicating the changed element values to a remote site for storage.

Viewed from a ninth vantage point, it is an object of the present invention to provide a device for compressing measurement data correlative to machine status, said device comprising in combination: at least one sensor operatively coupled to a machine for sensing data correlative to machine status; sampling means operatively coupled to at least said one sensor for sampling said sensed data into discrete elements; processor means operatively coupled to said sampling means for transforming said discrete elements into spectral elements and converting said spectral elements into magnitude and phase elements; means for defining intervals of magnitude and phase elements; means for storing a current interval of magnitude and phase elements; means for comparing a subsequent interval of magnitude and phase elements with said current interval of magnitude and phase elements; means for storing only said elements from said subsequent interval which are anomalous because they differ by a criteria from comparable elements of said current interval of elements wherein compressed measurement data correlative to machine status is continuously captured.

These and other objects will be made manifest when considering the following detailed specification when taken in conjunction with the appended drawing figures.

DESCRIPTION OF PREFERRED EMBODIMENTS

Figure 1:
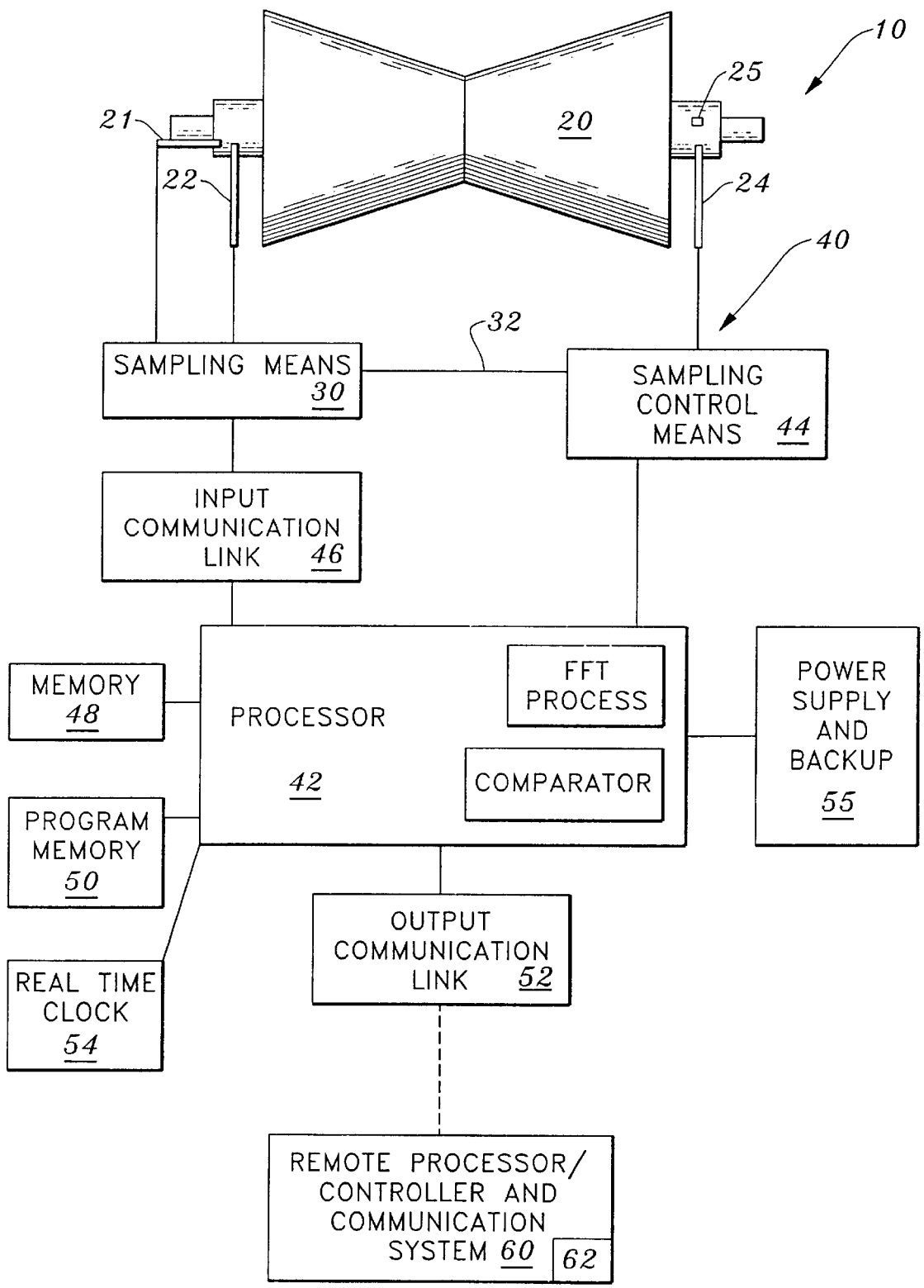
FIG. 1 is a diagrammatic view of a system according to the present invention.

Considering the drawings, wherein like reference numerals denote like parts throughout the various drawing figures, reference numeral 10 is directed to the system according to the present invention.

In essence, and referring to FIG. 1, the system 10 includes a computational means 40 operatively coupled to a sampling means 30 and a host computer or a remote processor/controller and communication system 60. The sampling means 30 is operatively coupled to at least one sensor 22 which in turn is removable or rigidly coupled to a machine 20 for sensing raw dynamic machine data correlative to machine status. The sampling means 30 is adapted to receive and sample the dynamic machine data under the orchestration of the computational means 40. The sampled data is communicated to the computational means 40 which transforms periods of sampled data into a periods of spectral elements while continuously collecting samples from the sampling means 30. At the outset, a first period of sampled data is transformed into a first period of spectral elements which are compared to a criteria and those which pass this criteria are stored in a memory means 48 along with at least one unique identifying tag associating an element number and a real-time valve of occurrence to each stored spectral element. In addition, the first period of spectral elements can be transmitted to and stored in a host computer 60 along with at least one unique identifying tag associating an element number and a real-time valve to each transmitted spectral element.

The computational means 40 receives and transforms each subsequent period of sampled data into subsequent periods of spectral elements which are in turn compared to the dominate criteria and those which pass are compared to the previous period of spectral elements which have been previously stored in the memory means for determining any anomalous behavior between the two. Preferably, only those elements included in each subsequent period which are anomalous are used to replace the corresponding data in the previous period of spectral elements for creating a new period used for comparing further subsequent periods. In addition, only those elements included in each subsequent period which are anomalous with respect to the previous period are transmitted to and stored in the host computer 60 along with at least one unique identifying tag associating an element number and a real-time valve to each transmitted spectral element.

The host computer 60 can then recreate a continuous waveshape correlative to the original raw dynamic machine data at any given time in history by, for example, using the anomalous spectral elements stored for that time and sequencing backward through the stored spectral elements sets to capture and use only those elements which have a different element number then the anomalous spectral elements and which are needed to form the original dominant spectral content. Therefore, the system 10 provides a significant improvement in data compression, the consumption of memory needed to store data for extended periods of time and the time needed to transmit this data to the remote host computer 60.

Figure 2:
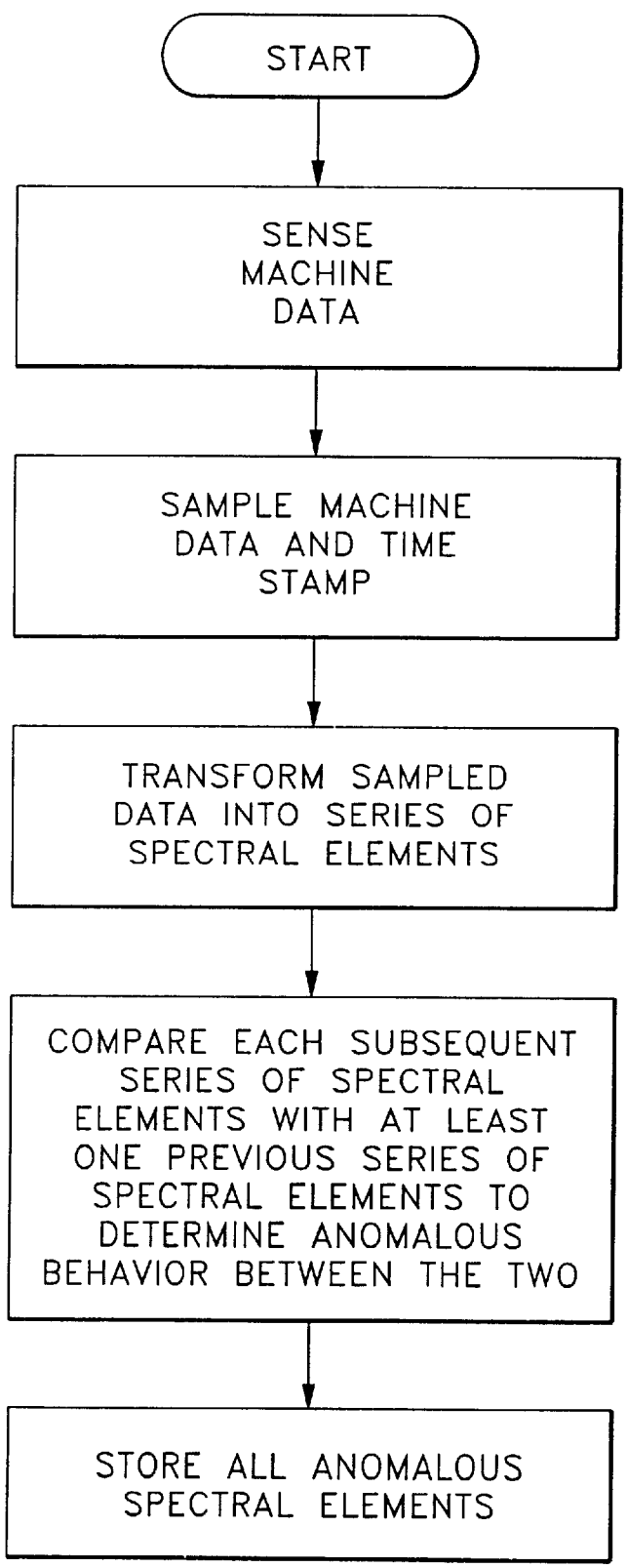
FIG. 2 is a general block diagram of a method according to the present invention.

More specifically, and referring to FIGS. 1 and 2, the system 10 is operatively coupled to at least one vibration sensor 22. The vibration sensor 22 is coupled to the machine 20 for monitoring the vibration of a machine casing, a rotating member or other structural motion associated with the machine 20. The vibration as seen by the vibration sensor 22 is related to the energy in the system imparted by the rotating element or other structural motion of the machine and is modified by the constraints of the other mechanical elements of the machine 20. The output of the vibration sensor 22 is a continuous electrical representation of the motion or the rate of change of the motion of the machine 20. The system 10 could also employ a plurality of sensors to operate independently or simultaneously to monitor the status of the machine 20.

In addition to at least the one vibration sensor 22 a phase sensor 24 is preferably operatively coupled to the machine 20 for sensing a mechanical phase reference mark 25 on, for example, a rotating shaft of the machine 20. This mark 25 is preferably used to relate the mechanical angle of the rotating shaft to the electrical signals of the sensor 22. For example, and referring to FIG. 9, the electrical signals S outputted by the sensor 22 (and/or sensor 21) can be marked with a point P each time the reference 25 is sensed by the sensor 24 which, in this example, is once per revolution of the shaft. Thus, creating a mechanical (zero degree) phase reference mark used to relate the mechanical angle of the rotating shaft to the electrical signal S outputted by the sensor 22 and to a correlative signal S' reconstructed from compressed electrical signals S (please see FIG. 10). The electrical signals from the phase sensor 24 are input to a sampling control circuit 44 which will be delineated infra.

The sampling means 30 is operatively coupled to the sensor 22 and is adapted to receive the electrical signals from the sensor 22. The sampling means 30 converts the signals into digital values at intervals established by the sampling control means 44 instigating a sample through a control line 32. The sampling control means preferably includes means for providing both synchronous and asynchronous timing pulses and specifically, synchronous and asynchronous timing pulses correlative with respect to machine speed. The output of the sampling means 30 is a series of digital values representing the instantaneous value of the sensed electrical signals at the time the control line 32 instigates the sampling of the sensed electrical signals outputted by the sensor 22. A typical embodiment of the sampling means 30 is an analog to digital converter.

The computational system 40 includes a processor 42, including a digital signal processor means, operatively coupled to the sampling means 30 via a input communication interface 46 for receiving the series of digital values representing the raw vibration machine data sensed by the sensor 22. The sampling control means 44 is operatively coupled to and interposed between said sampling means 30 and said processor 42 for controlling the sampling rate of sampling means 30.

The computational system 40 further includes the memory means 48, a program storage means 50, an output communication interface 52 and a real time clock 54. The computational system 40 employs the real time clock 54 for uniquely tagging each digital value with a real time value for identifying a time in history of when the corresponding instantaneous value of the signal was captured from the sensor 22 and can also be used to provide a real time value for identifying sampling rates of the sampling means 30. Processor 42 further includes a fast fourier transform algorithm (FFT) which can be stored in the program memory 50. Generally, and referring to FIG. 2, the FFT algorithm transforms a first set of digital values into a first series of spectral elements while the processor 42 continuously collects digital samples from the sampling means 30. A subsequent set of digital values is transformed into a subsequent series of spectral elements which are compared to the first set of spectral elements which have been stored in memory means 48. The processor 42 includes means for comparing the first series of spectral elements with the subsequent series of spectral elements and determining any anomalous behavior between the two and/or comparing the first series and subsequent series of spectral elements with a user definable criteria. The computational system 40 further includes an output communication interface 52 operatively coupled between the processor 42 and the host computer 60 for transmitting the anomalous digital values to the host computer 60 where, for example, they are stored in a historical data base 62. The output communication interface 52 can take the form of, inter alia, wire, fiber optics, networks, radio frequency (RF) links, internet links, microwave links and satellite links. In addition, since the data is preferably time tagged it can be sent in brief bursts from a collection site (computational system 40) to a remote site (host computer 60) and then reconstituted.

Preferably, the sampling control means 44 has two modes. The first mode issues electrical commands to the sampling means 30 from the sampling control means 44 to sample the vibration signal in discrete time increments which can be controlled by the processor 42. In this mode each sample is spaced apart by a predetermined amount of time. For machine management with an upper frequency of interest of 20 kilohertz, data collection can take 20 milliseconds (1024 samples at a 51.2 kilo sample/second rate).

In a second mode the samples are taken at discrete phase increments. A typical phase increment of 11.25 degrees results in data collection in no less than 32 milliseconds (1024 samples taken 32 samples each revolution of the shaft to a maximum speed of 60,000 RPM). These signals are preferably generated by taken the period of the once per turn phase reference signal generated by the phase sensor 24, dividing by the number of samples per revolution and causing a sample signal from the sampling control means 44 to the sampling control line 32 at this shorter period.

Figure 3:
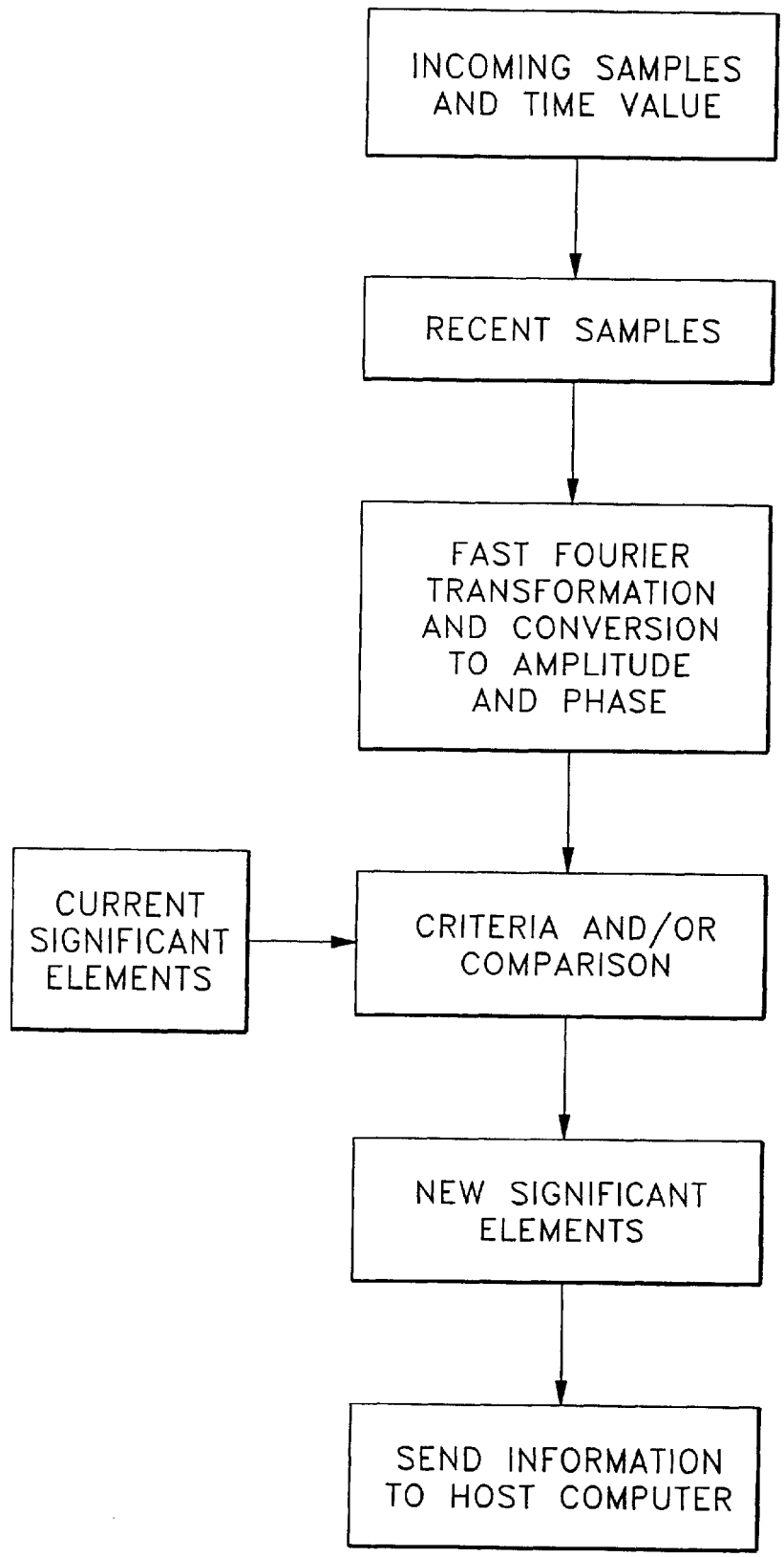
FIG. 3 is a block diagram detailing a method of compressing measurement data correlative to machine status according to the present invention.
Figure 4:
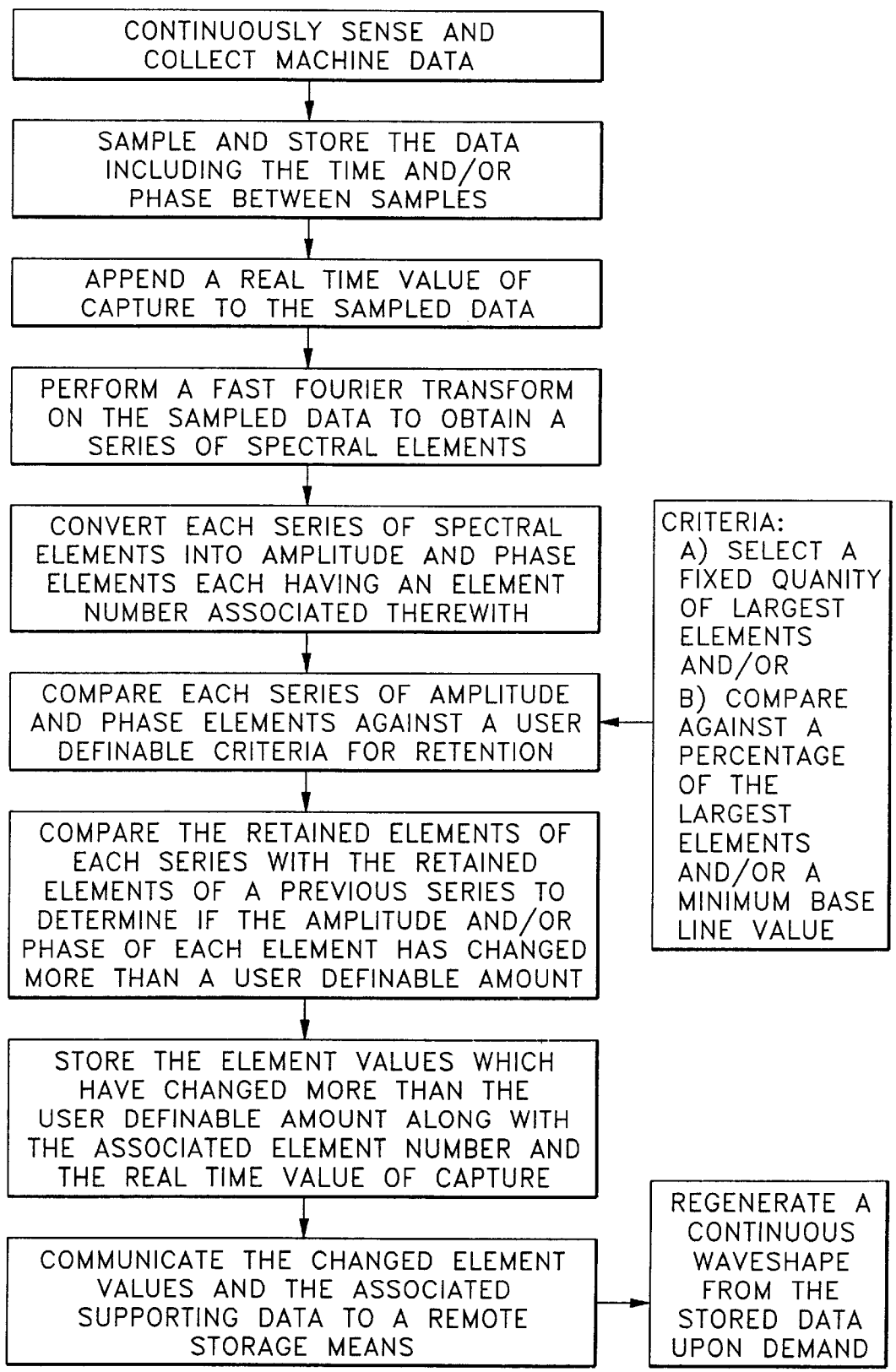
FIG. 4 is a block diagram specifically a method of compressing measurement data correlative to machine status according to the present invention.

Still more specifically, and referring to FIGS. 1, 2 and 3 the system 10 performs a series of operations on the incoming digital stream of vibration data samples transmitted from the sampling means 30 to the processor 42. The incoming digital stream of vibration data samples are temporarily stored in memory 48 along with the sampling rate or the real time value or phase representing the time or phase between adjacent samples. After a first set of samples is gathered, the processor 42 using a fast Fourier transform algorithm processes the set. Simultaneously, digital data samples continue to be collected while processing is conducted on the first set of data and subsequent sets of data. Each sampled data set which is processed by the processor 42 results in a data set of spectral elements representing the sine and cosine convolution of the data. The elements in each data set are then preferably converted to amplitude and phase elements. Thus, both amplitude and phase data is available for future comparison and ultimately signal reconstruction.

Furthermore, at least one unique identifying tag associating an element number and a real-time valve of occurrence is associated with each spectral element. The unique real time value can be obtained from the real time clock 52 and is used, inter alia, to identify the real time in which the data was captured. Typically, this time can be collected with a resolution of one millisecond.

In a highly cyclic input, the significant information is contained in dominant spectral components, with the lower amplitude and non-harmonic components resulting from discontinuities due to electrical sampling, electrical noise or mechanical or electrical run out sensed by the vibration sensor.

The criteria for determining dominant spectral components of any element or series of elements can be based on a user definable criteria. The user definable criteria includes using a fixed number of spectral lines, using a minimum level above which values are dominant, using a level related to the highest spectral line or any combination of these criteria. Thus, the present invention simultaneously reduces data volume and eliminates noise. Preferably, compression is realized by only transmitting and saving the spectral lines that have changed by an established percentage or value since the last reporting to the host computer and when these changes occurred. Thus, the host computer 60 can regenerate continuous wave shapes from the dominant spectral content for any given time by performing an inverse Fourier transform and displaying the resultant wave shapes on a computer display.

Specifically, the determination of the dominant spectral content of each set of the spectral elements is accomplished by using a user definable criteria for retention. This criteria can be applied in a number of different ways. One preferable method is to select a fixed quantity of the largest elements. These dominant elements are compared against the dominant elements determined in a previous fast Fourier transform computation. If the magnitude or phase of a single element has changed more than a user definable number picked for the percentage change, then the new element value is stored in memory and the element number and time is noted for transmission to the host computer 60. All the elements that do not fall in the quantity of the largest elements are ignored.

Alternatively, a second preferred method for the criteria for retention retains the element if the element is greater than a fixed percentage of the largest element and/or greater than a base line element magnitude. Any element which is larger than a user definable percentage of the largest element is retained as long as it is larger than a minimum value. It has been discovered that as the signal approaches zero, noise values predominate (i.e. white noise or a flat spectral distribution). Thus, the minimum element magnitude is selected to be slightly larger than the noise spectral amplitudes and if they are less than the noise spectral amplitude they are discarded. Note that in this method, the number of elements that qualify for retention can vary.

The last operation is to communicate those elements to the host computer which have passed the selection criteria. If no elements have changed sufficiently to meet the criteria to notify the host than no transmission takes place and the host knows that the values which are presently held for subsequent elements are valid for the elements for that time as well. If only one element of a larger number has changed than it is the only one reported to the host computer as having been changed.

The output communication interface communicates the changed elements to the host computer 60. The transmission data includes a sample time, an element number and a real time value for each element and the corresponding magnitude and phase of each element. This data may be sent in any format.

Once the host computer is provided with the elements of the fourier transform, it can recreate the values of the sampled sets using an inverse fourier transform. For example, if we know the content of the elements of the vibration at any time we can recreate the waveshape at that time.

The present invention makes it possible to take continuous sample data sensed from a running machine, perform a Fourier transform and collect and store only those elements which are significant and only those elements which changed since the last stored values. In addition, the present invention makes it possible to reconstruct continuous signal at any time by also storing the time that the value changed and information regarding the sample rate of the signal. Furthermore, the compression method of the present invention is a lossy technique and thus, once the data is compressed the original signal cannot be recreated exactly. However, the compression technique of the present invention is highly effective because it only retains the significant content of the data and it only stores the data if it has changed.

Synchronous Sampling

The vibration of rotating machinery tends to be based on the speed of the machine. Thus, and as mentioned supra, the sampling means 30 can sample the raw dynamic machine vibration signal or waveform into discrete digital values synchronously with machine speed monitored via sensor 24. For rotating machinery, sampling the waveform over an integer number of revolutions forces synchronous vibration components to be commensurate thereby improving both the amount and accuracy of the compression methods of the present invention.

The processor 42 transforms the sampled waveforms with a Fast Fourier Transform (FFT) algorithm. When the Fast Fourier Transform (FFT) processing is preformed it is preferably done over an integer number of revolutions and ideally, one wants to end and start at the same point on the waveform because the FFT views the waveform as being continuous. As a result, and referring to FIG. 13, by taking the FFT of a vibration signal or waveform between, for example, points P1 and P2 results in a spectrum that has far less elements or filled bins than by taking the FFT of the vibration signal or waveform between, for example, points P1 and P3.

Figure 14:
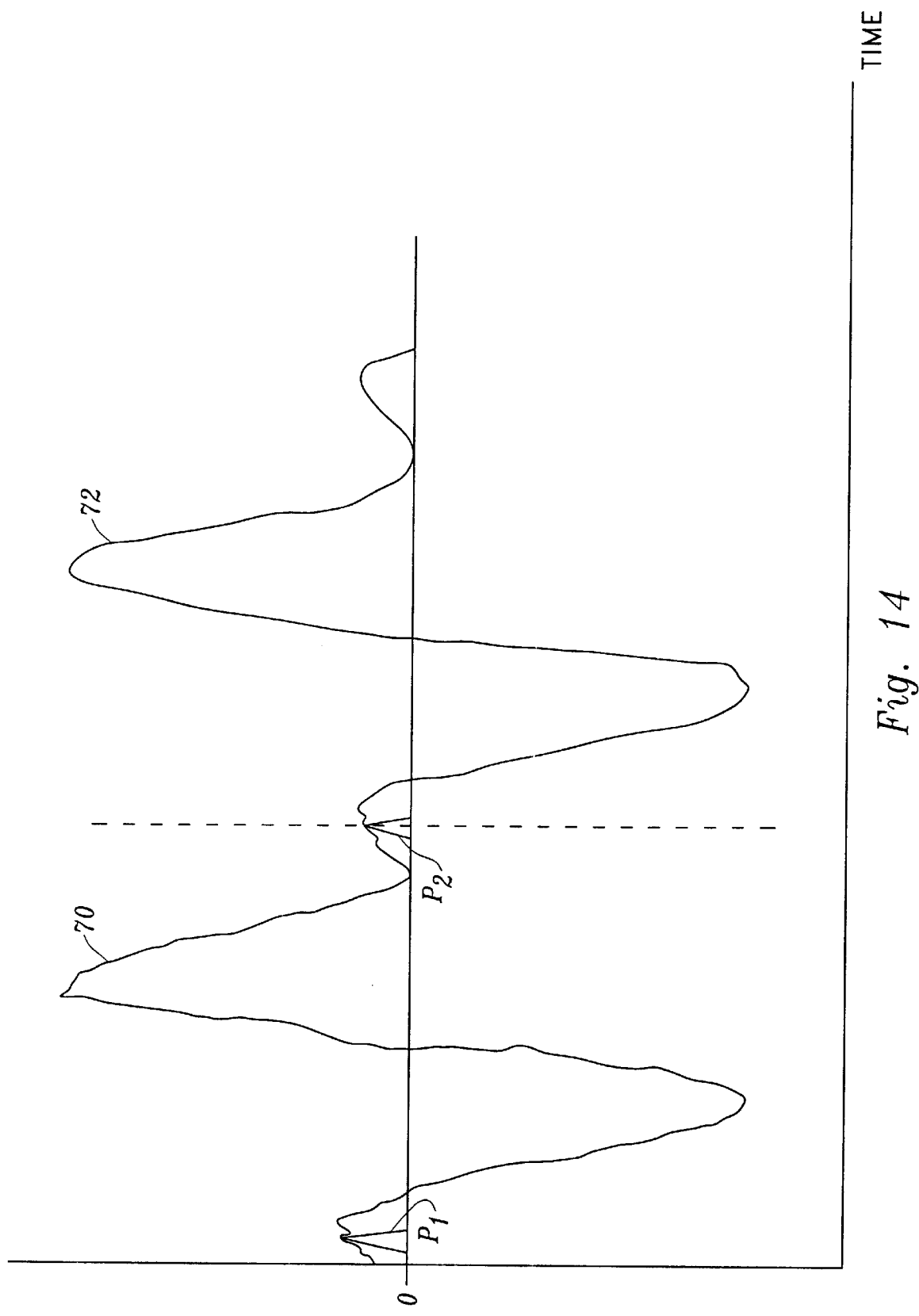
FIG. 14 is a graphical representation of a commensurate vibration waveform and its reconstruction after being compressed according to the present invention.
Figure 15:
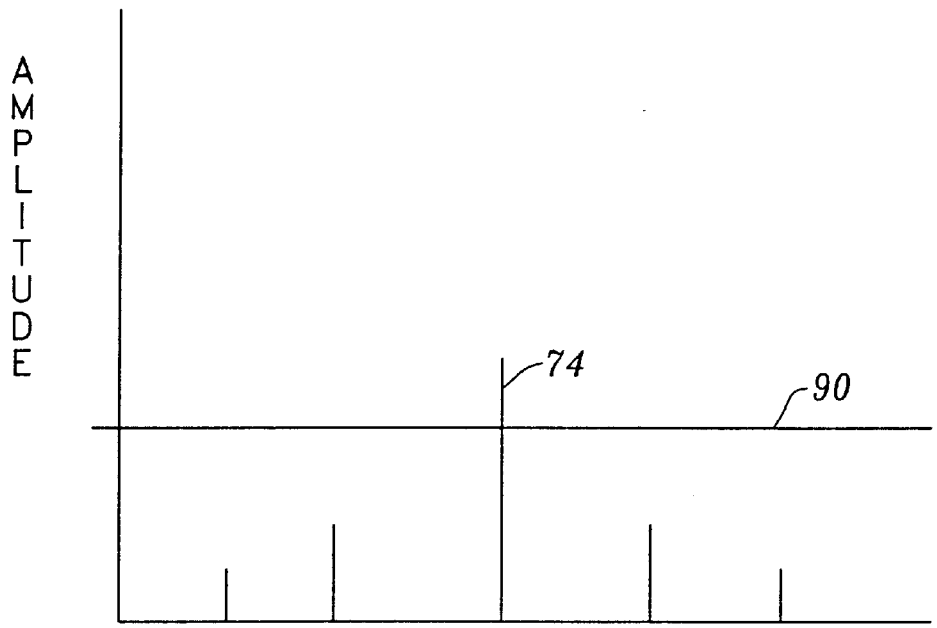
FIG. 15 is a graphical representation of a spectrum plot of a commensurate vibration waveform and a criteria baseline value.
Figure 17:
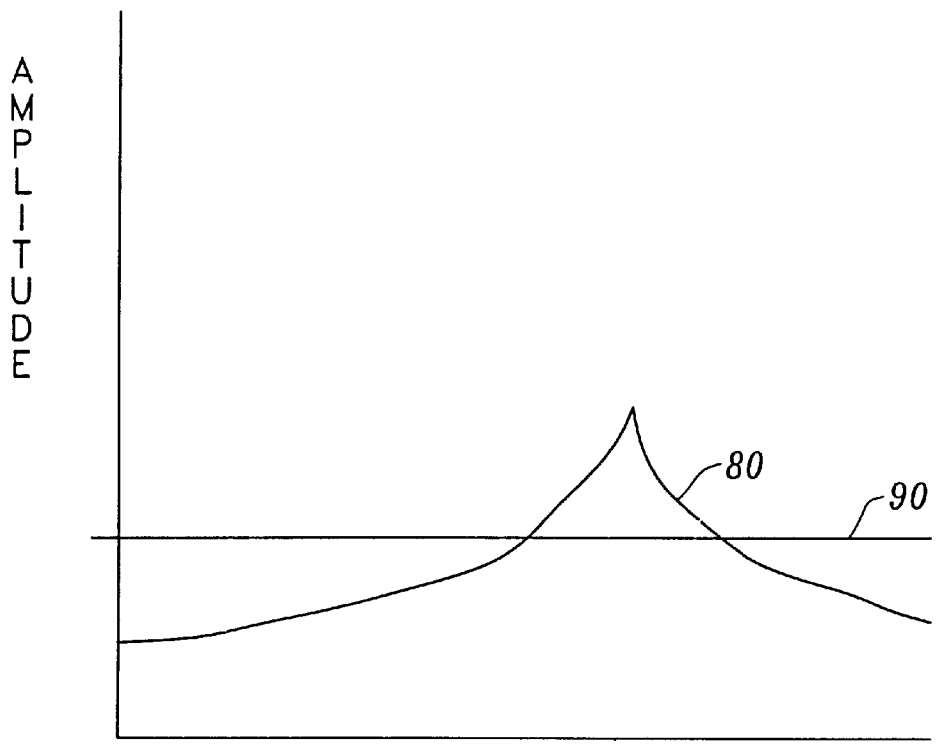
FIG. 17 is a graphical representation of a spectrum plot of an incommensurate vibration waveform and a criteria baseline value.
Figure 18:
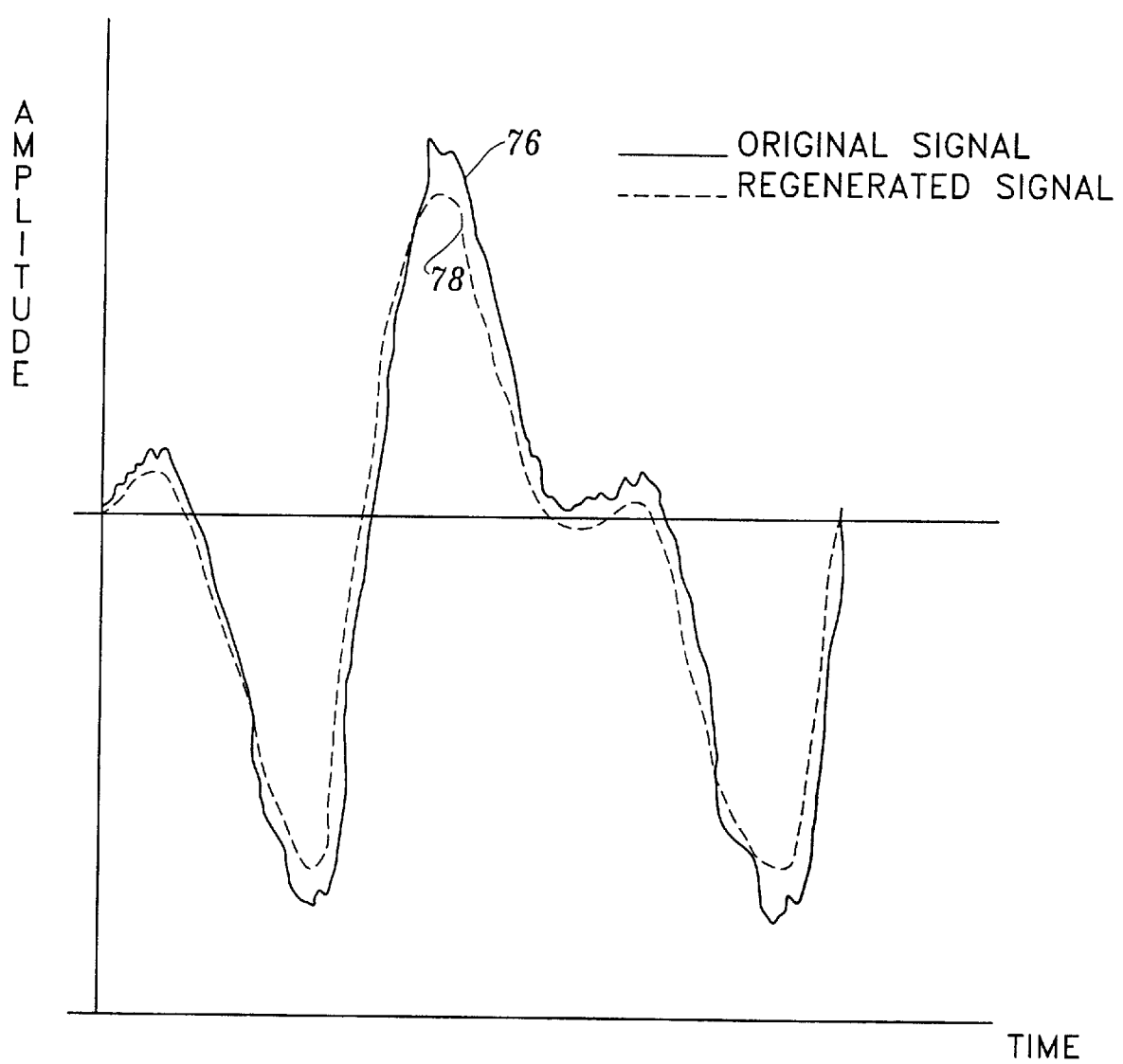
FIG. 18 is a graphical representation of an incommensurate vibration waveform and its reconstruction after being compressed according to the present invention and showing how the reconstructed waveform pull in from the original.

Accordingly, and referring to FIG. 14, if one has a commensurate waveform 70 defined between points P1 and P2, what the Fast Fourier Transform processing reconstructs is waveform 72 which may include only one spectral element 74 or one filed bin in the spectrum that rises above a defined criteria level or baseline value 90 as is shown in FIG. 15. In stark contrast, and referring to FIG. 16, if one has an incommensurate waveform 76 defined between points P1 and P3, what the FFT processing tries to reconstruct is waveform 78 which includes a large number of spectral elements 80 that rise above the baseline value 90 as is shown in FIG. 17. Thus, the incommensurate waveform 76 results in there being many more spectral elements or filled bins that rise above the baseline value 90 than that which rise above the baseline value 90 for the commensurate waveform 70. As a result of waveform 76 being incommensurate it tends to pull in from the original waveform and become distorted when reconstructed as illustrated by waveform 78 depicted in FIG. 18.

Figure 9:
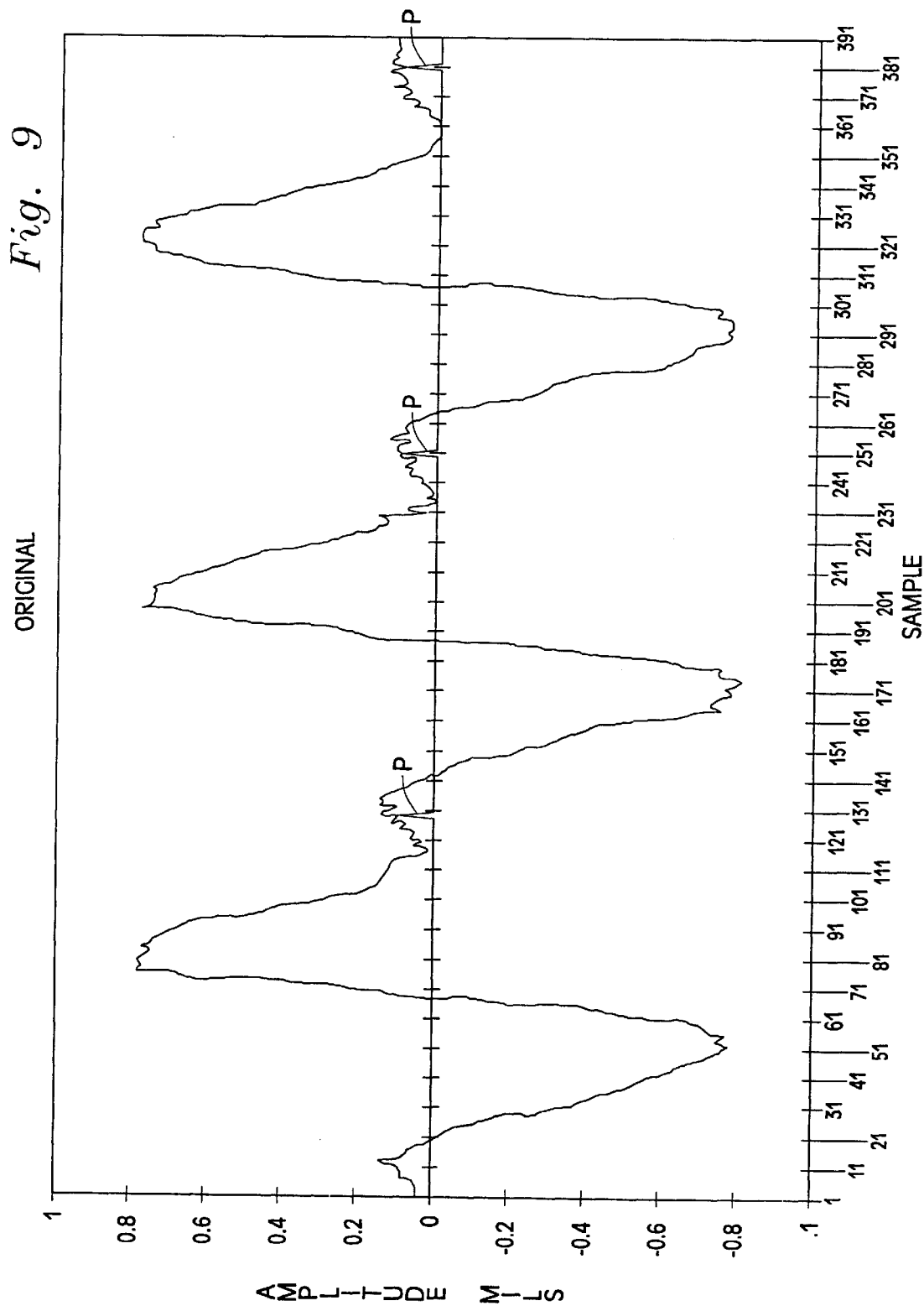
FIG. 9 is a graphical representation of continuous vibration signals sensed by a vibration sensor and mechanical phase reference marks sensed by a mechanical phase sensor.
Figure 13:
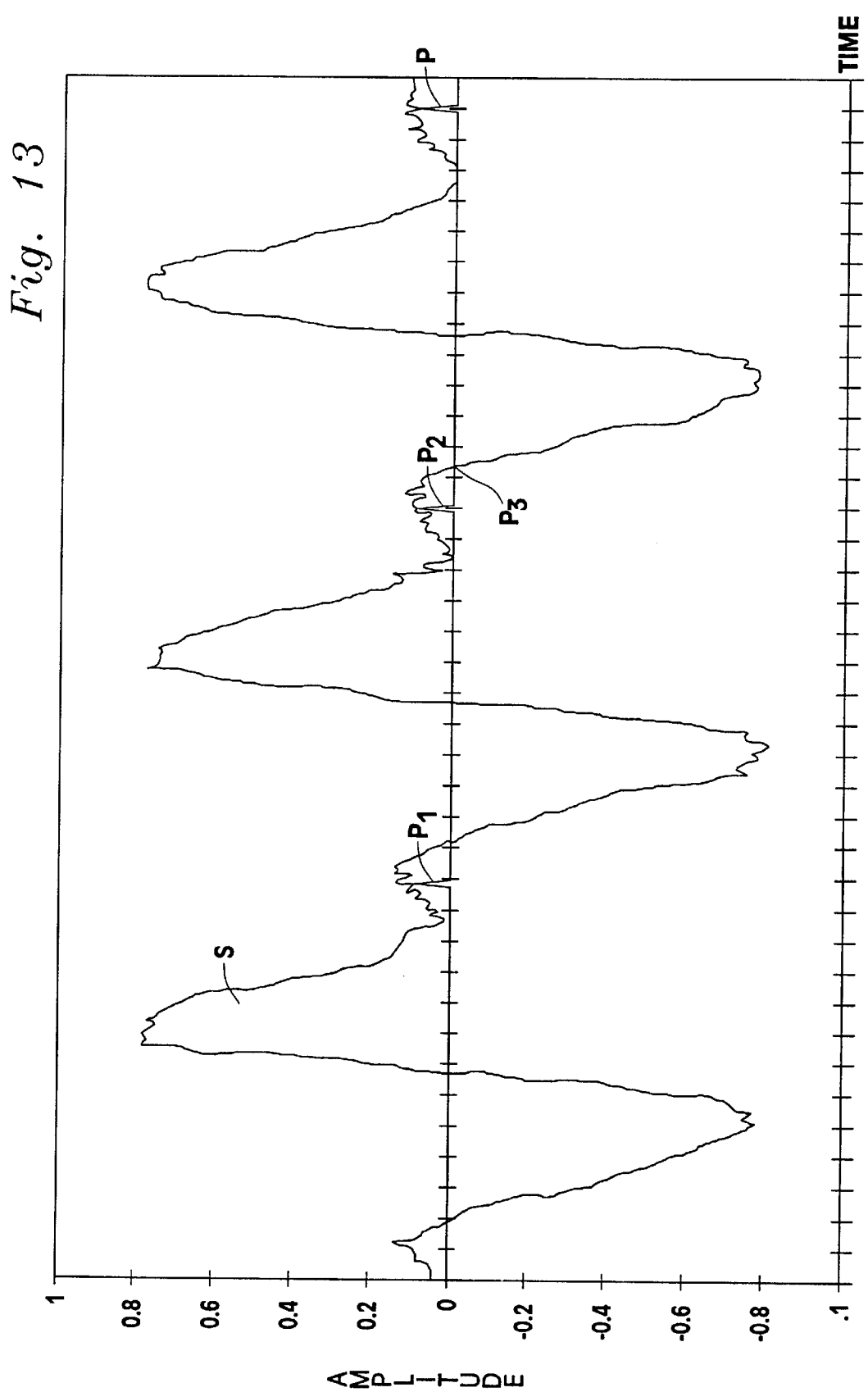
FIG. 13 is a graphical representation of continuous vibration signals sensed by a vibration sensor, mechanical phase reference marks sensed by a mechanical phase sensor and points P1, P2, P3 for representing commensurate and incommensurate waveforms.

The present invention reduces this distortion by sampling vibration signals synchronously with machine speed thereby resulting in waveforms that are sampled in a commensurate manner (sampling starts and ends at the same point) as shown in FIGS. 9 and 13.

Figure 19:
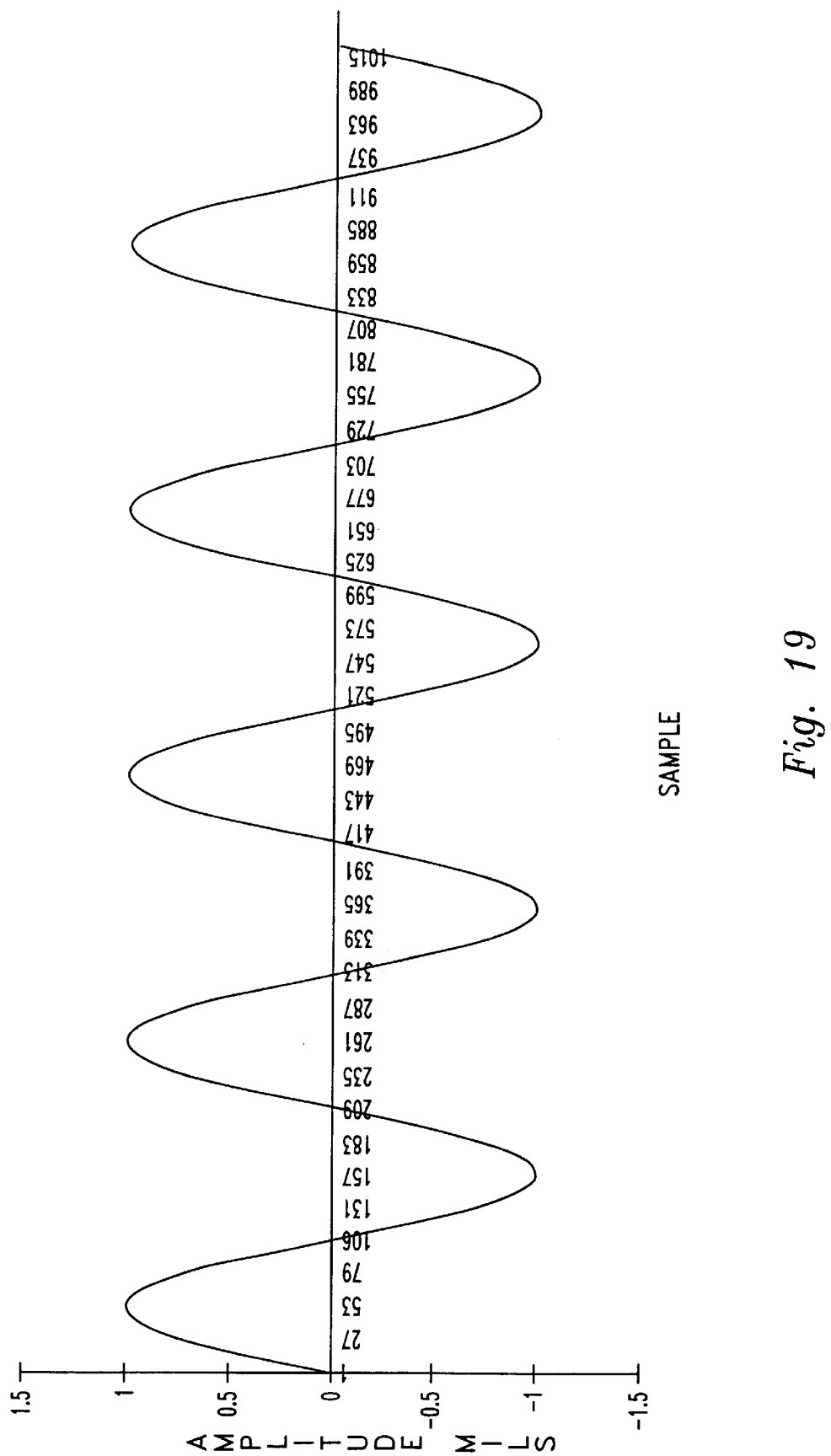
FIG. 19 is a graphical illustration of a commensurate waveform divided into one thousand twenty four sampling intervals.
Figure 20:
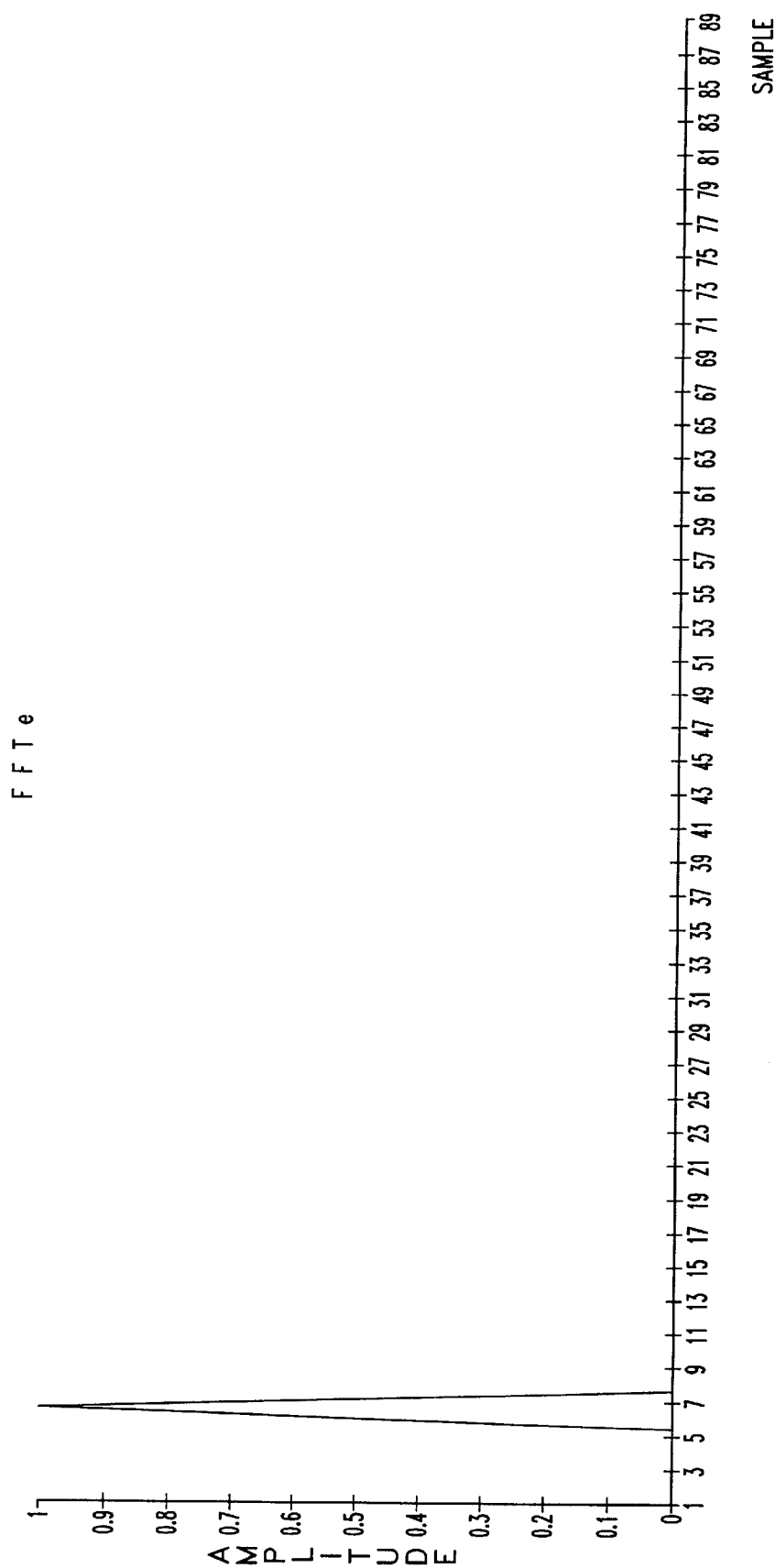
FIG. 20 is a graphical illustration of a of a spectrum plot of the commensurate waveform shown in FIG. 19.
Figure 21:
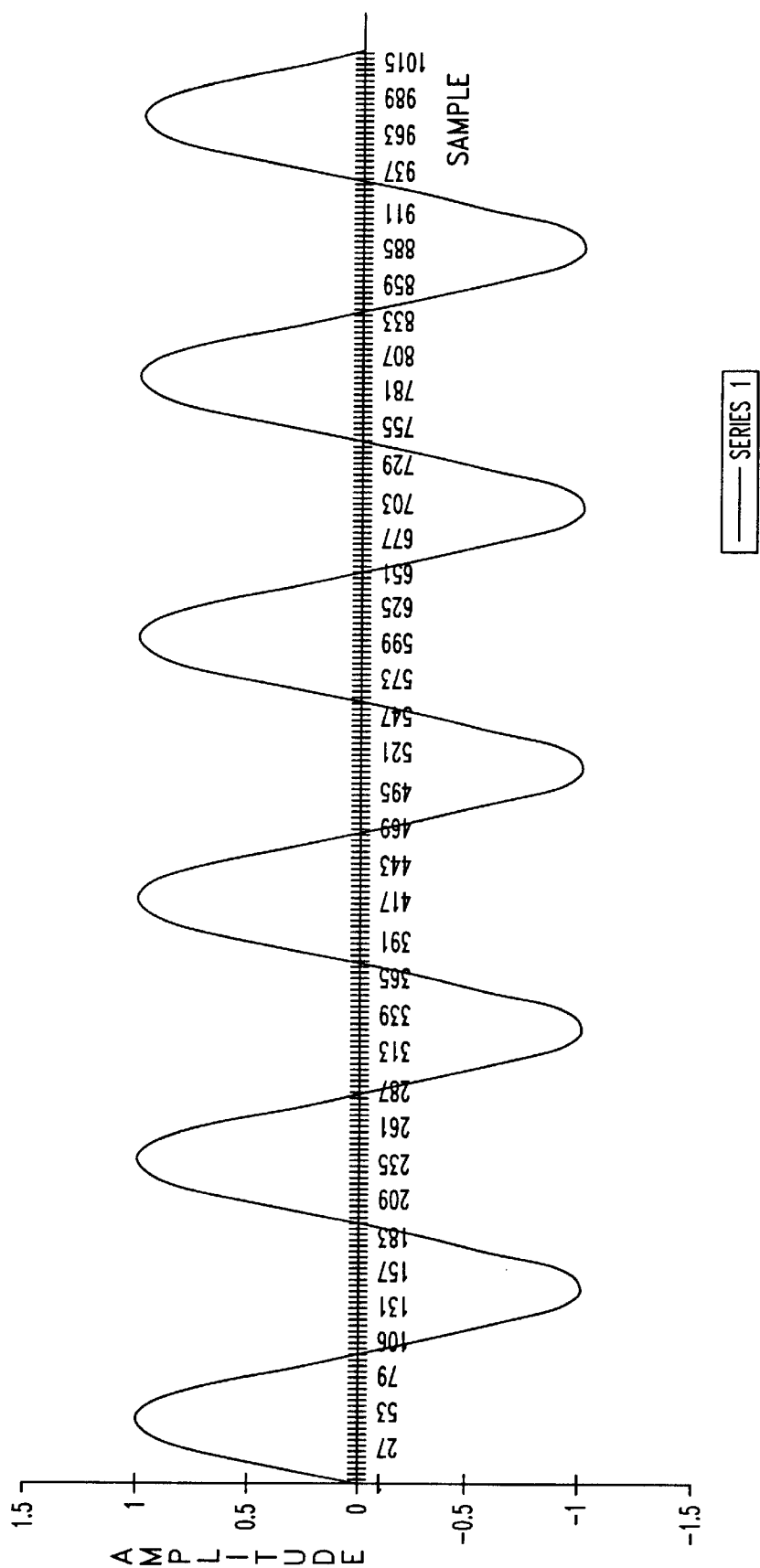
FIG. 21 is a graphical illustration of an incommensurate waveform divided into one thousand twenty four sampling intervals.
Figure 22:
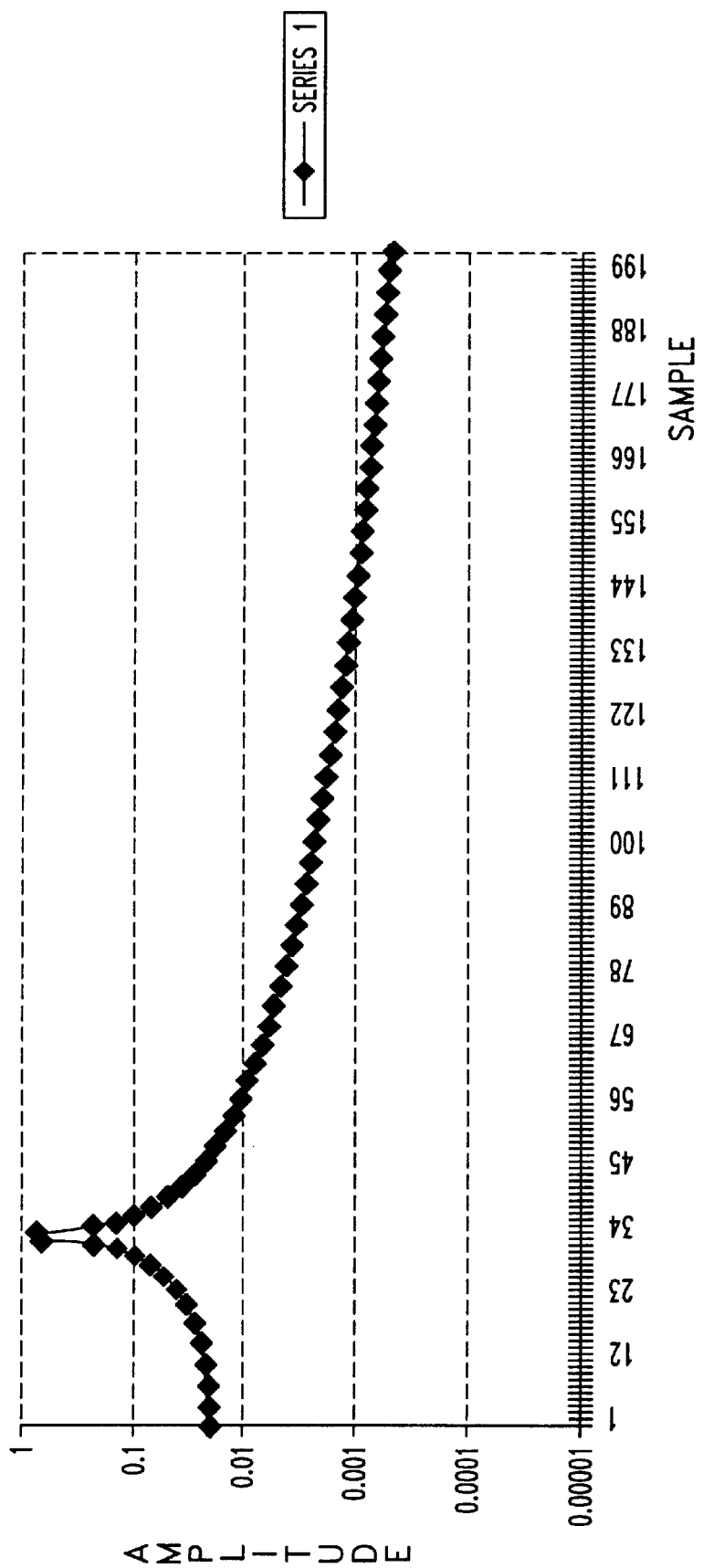
FIG. 22 is a graphical illustration of a of a spectrum plot of the incommensurate waveform shown in FIG. 21.

FFT processing works well for extracting information from commensurate waveforms such as that illustrated in FIG. 19 by requiring a few spectral elements for its representation as illustrated in FIG. 20. In contrast, an incommensurate waveform such as that illustrated in FIG. 21 requires many spectral elements its representation as illustrated in FIG. 22. Accordingly, a much higher and more accurate compression level is obtainable from sampling commensurately as opposed to sampling incommensurately. Thus, the combination of the present invention recognizing that machinery vibration is primarily made up of distinct spectral elements or components, sampling commensurately, recording and storing the frequency, real and imaginary components or amplitude and phase components of each of these distinct spectral elements and only transmitting this information as opposed to transmitting the whole waveform results in a high compression level of vibration waveforms.

In summary, a majority of vibration signals of rotating machinery are synchronous to the rotation of its shaft. Thus, if the raw dynamic vibrations signals are sampled over an integer number of revolutions it is highly likely the resulting sampled signals will be commensurate. This leads to FFT processing that has few components as illustrated in FIG. 20, which in turn increases the probability of high compression. In other words, sampling the incoming sensor or transducer data based on an integer number of revolutions results in an increase in the probability of the data being sampled commensurately and subsequently improving data compression.

Figure 23:
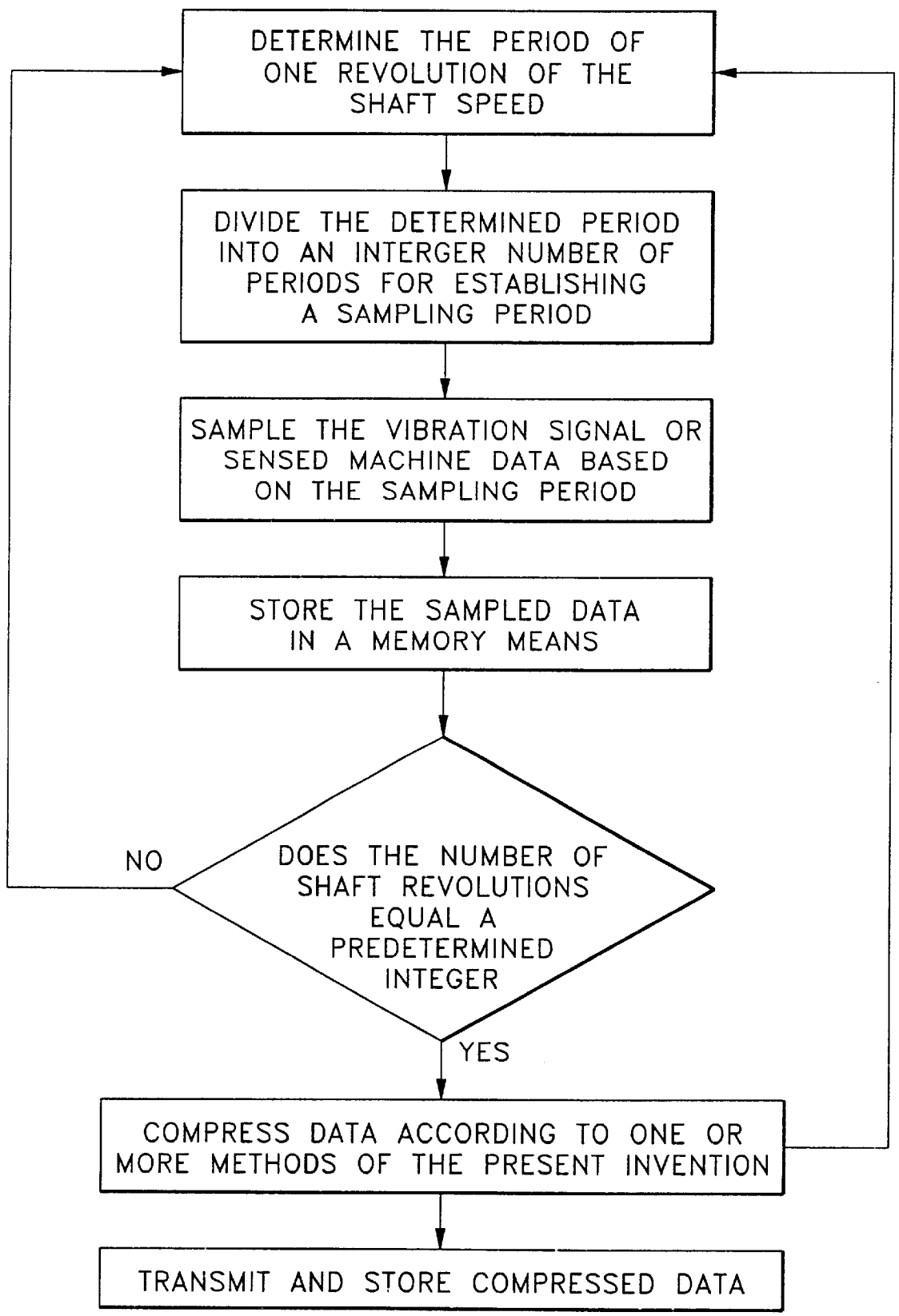
FIG. 23 is a flow chart of a method for providing synchronous sampling according to the present invention.

As shown in FIG. 23, the following steps outline one method according to the present invention for providing synchronous sampling for improving the compression techniques according to the present invention.

1. Determine the period of one revolution of the Shaft Speed.
2. Divide the measured period of one rotation into an integer number of periods to establish the sampling period.
3. Sample the vibration signal based on the sampling period.
4. Take an integer number of shaft revolutions of data adjusting the sample period after each revolution using steps 1 through 3.

5. Process the data using one or more of the compression methods according to the present invention.

Period Prediction Methodology

Utilizing synchronous sampling produces great improvements to compression technique and the process delineated above works well if the machine always rotated at the same rate (constant speed or RPM). In that case, one could determine the constant rate and always sample at the determined rate but it would be done so under the assumption that the speed of the machine for the most recently sampled period is the same as that of the present period. However, this is typically not the case and a change in machine speed results in the sampling becoming incommensurate. Thus, as machine speed varies an incommensurate sampling rate is engendered as a result of the period of rotation for the present period not being the same as the previous period.

A better estimate of the correct sampling rate can be determined by utilizing a period prediction method that improves the ability to track changing RPM. This method determines the past rate of acceleration and applies that rate of acceleration to the present measured rotational period to predict the next future period. The following process describes the use of a first order method using one previous and one current period to predict the next period. Using more previous periods can provide higher order approximations.

In essence, the present invention determines the RPM of a plurality of consecutive periods that are immediately previous to the next period being sampled and then determines the acceleration or deceleration of the machine from these consecutive periods. This determined value is utilized to predict the RPM of the machine for the present period. For example, if the determined value reveals that the machine speed increased by ten percent then the system 10 can predict that the present RPM is ten percent greater than the RPM of the last period or revolution or may scale this percentage based on empirical data. The key is that the present invention uses the RPM of previous periods to predict the RPM of the present period being sampled for providing commensurate sampling and thus improving data compression.

This period predication method can be thought of as a moving period predication window that captures the RPM of a plurality of consecutive or successive periods which immediately precede the present period being sampled so that the sampling rate of the present period can be dependent on the predicted RPM value for providing commensurate sampling.

More specifically, commensurate waveforms can become incommensurate when the sampling ceases too soon or too late. Thus, the system 10 utilizes the period predication method or moving period predication window for substantially maintaining commensurate sampling by using a predicted RPM that is always ahead of the measured RPM. Accordingly, this period prediction methodology is an important improvement in keeping the sampling commensurate, which in turn, improves data compression according to the present invention by limiting the number of spectral elements, components or filled bins.

Figure 24:
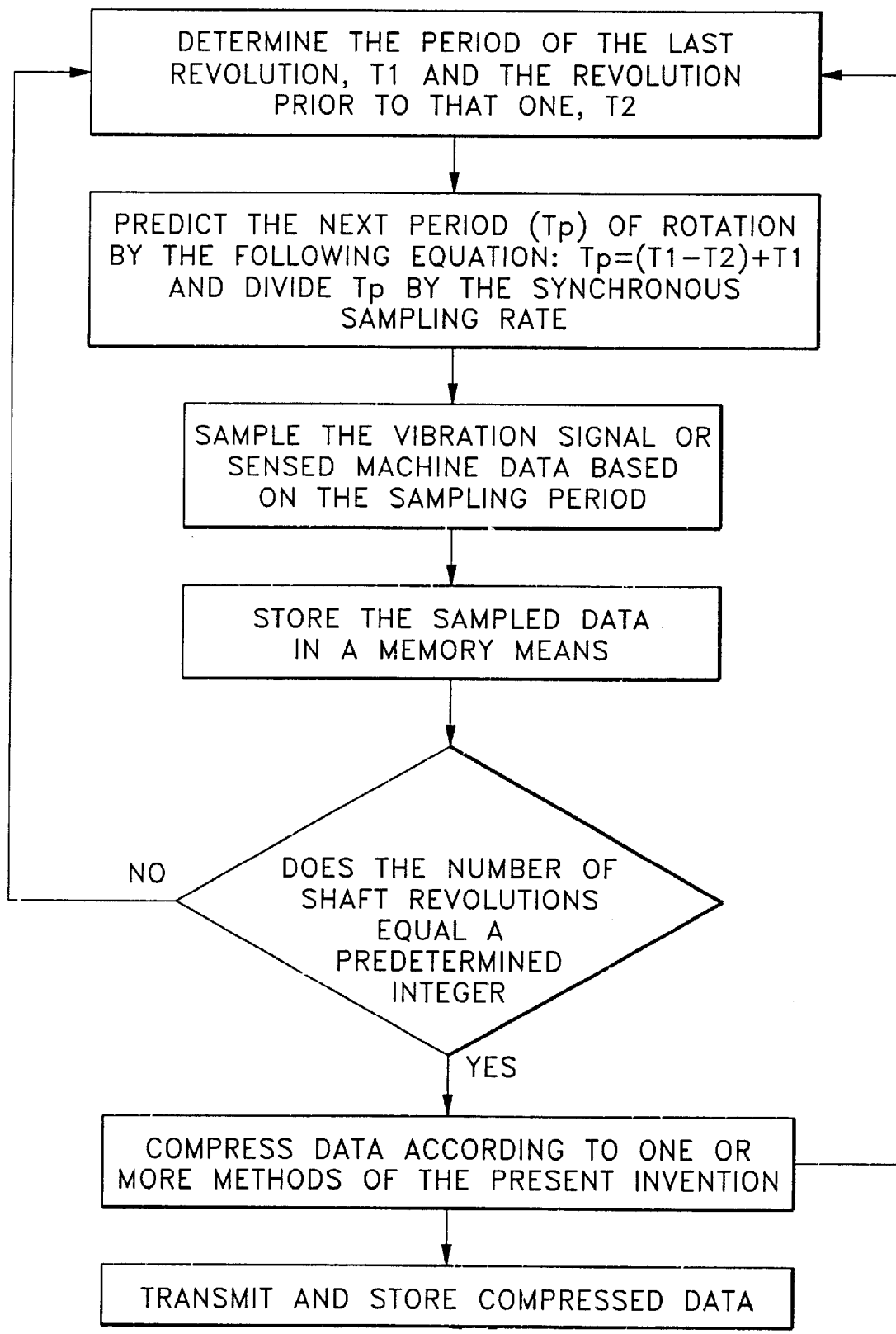
FIG. 24 is a flow chart of a method for providing period prediction according to the present invention.

As shown in FIG. 24, the following steps outline the period prediction method according to the present invention for improving the probability of obtaining commensurate sampling and improving data compression according to the present invention.

1. Determine the period of rotation of the last revolution, $T_1$ and the revolution prior to that one, $T_2$.
2. Predict the next period of rotation by the following equation: $T_p=(T_1-T_2)+T_1$
3. Determine the sampling period by dividing the period Tp by the synchronous sampling rate.
4. Sample the signal based on the new sampling period.
5. Take an integer number of shaft revolutions of data adjusting the sampling period each revolution using steps 1 through 4.
6. Process the data using one or more of the compression methods according to the present invention.

A further improvement, which is discussed infra, can be made by altering step 3 to create sampling intervals that vary during the revolution based on the rate of acceleration.

Multiple Event Per Revolution Period Prediction Methodology

The above period prediction methodology is assuming a first order acceleration or deceleration (synchronous change). In other words, the above period prediction method assumes the acceleration or deceleration during each shaft revolution is constant. This may not be the case. For example, if the frequency of the vibration signal increases our predicted RPM value may be inaccurate thereby resulting in a spectrum that spreads out or at least looks like two spikes.

The present invention solves this problem by using a multiple event per revolution period prediction methodology. This increases the rate at which information about the shaft speed comes into the system thereby improving the ability to provide commensurate sampling. The increased information rate can be accomplished by providing a multiple event per turn input into the system. The system then updates its sampling rate based on each new period provided by the multiple event sensor. Thus, the sampling rate can match the actual (and changing) machine speed more accurately and thus measure a more accurate synchronous representation of the signal.

For example, an encoder having an encoder wheel can be operatively coupled to the shaft such that the RPM is updated on a more continuous basis thereby allowing the system 10 to use the RPM from the encoder to rapidly predict the RPM and then use this to adjust the sampling during each measured fraction of a shaft revolution. Thus, if the shaft accelerated during any particular revolution the system would increase the sampling rate and conversely, if the shaft decelerated during any particular revolution the system 10 would decrease the sampling rate.

Thus, by using a speed wheel or optical encoder as a second timing input into the system, in addition to the once per turn input a better sampling rate can be obtained in relation to the shaft speed. This helps to keep the data commensurate and thus improves the compressibility of the data. Additionally, existing machine gears, reflective tape, lasers, bolts at the end shaft, et cetera are all examples of measuring the RPM of the shaft for providing multiple RPM readings during any particular revolution.

Even if a submultiple RPM reading were delayed it would still be advantageous in the predictive period methodology.

Figure 25:
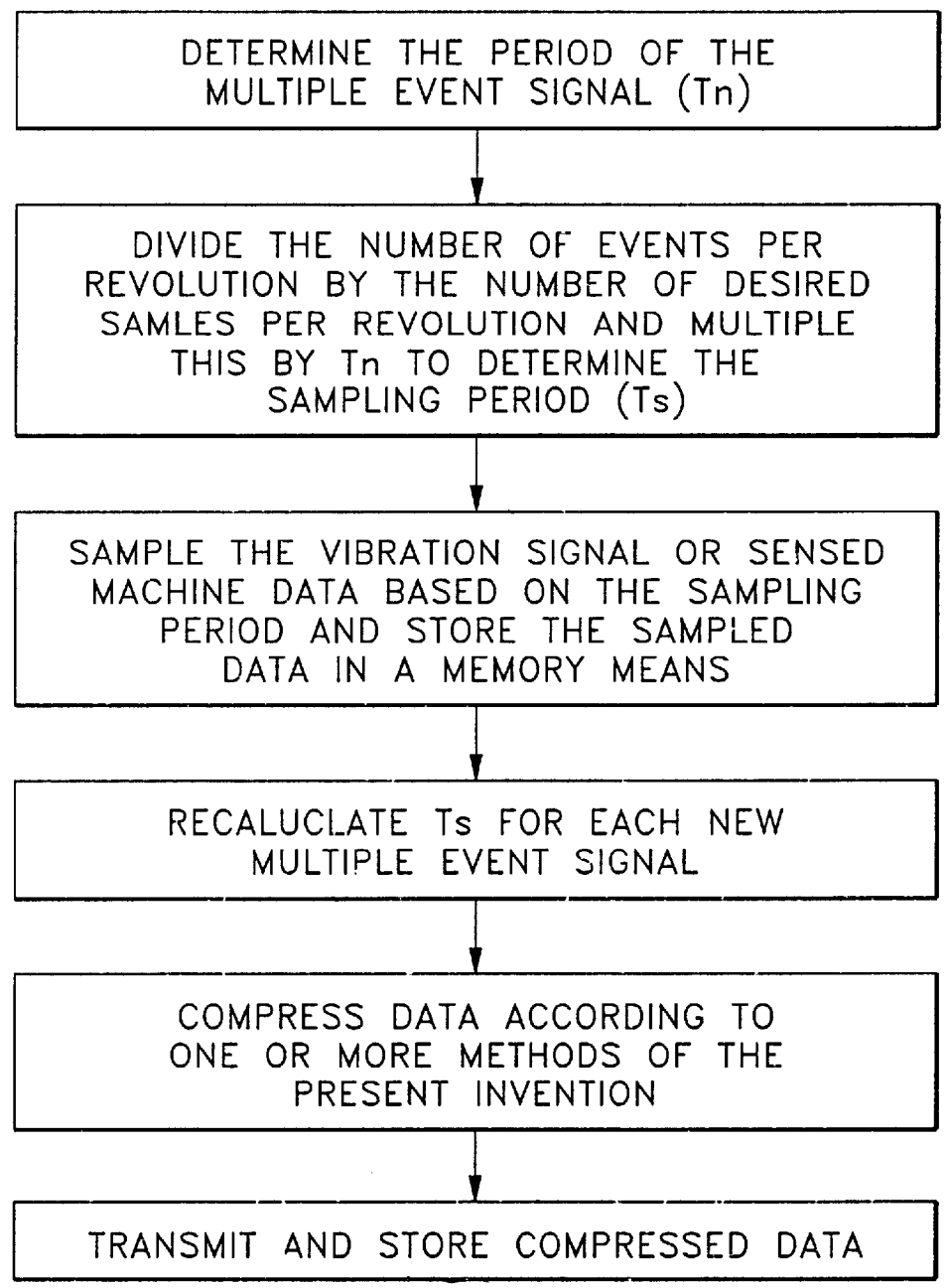
FIG. 25 is a flow chart of a method for providing multiple event sampling for according to the present invention.

As shown in FIG. 25, the following steps outline the multiple event per revolution period prediction method for improving the probability of obtaining commensurate sampling and improving data compression according to the present invention.

1. Measure the period of the multiple-event signal, $T_n$.
2. Determine the sampling period: $T_s=T_n*$(Number of Events Per Revolution/Samples Per Revolution).
3. Sample the signal based on the sampling rate $T_s$.
4. For each new multiple-event signal recalculate $T_s$ and apply it during the next sampling interval.
5. When the sufficient number of samples has been acquired process the data using one or more of the compression methods according to the present invention.

A once per turn signal or a counter to compare events to samples can be used to correct for any incremental error due to the resolution of the multiple events and the latency in adjusting the sampling rate.

Windowing Methodology For Asynchronous Sampling

In machine monitoring asynchronous data engendered from, for example, proximity and case mounted transducers is also sampled for determining phenomena associated with the rotation of the machine and also the phenomena based on the machine case or housing. Additionally, many systems do not have a speed signal or phase reference and only include a vibration sensor that samples at a continuous rate that is correlative to the highest frequency of interest.

Figure 16:
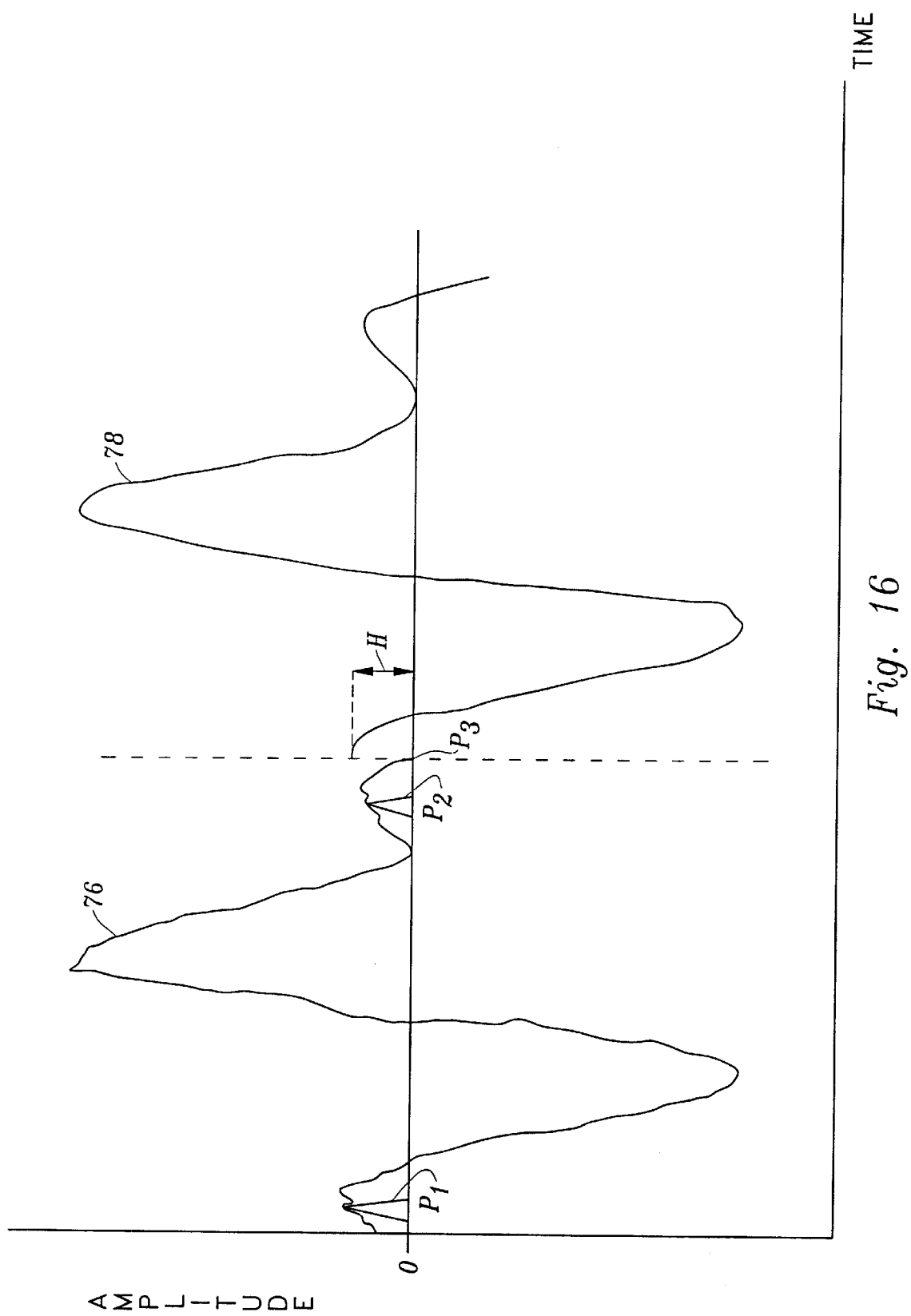
FIG. 16 is a graphical representation of an incommensurate vibration waveform and its reconstruction after being compressed according to the present invention.

Thus, this data is sampled asynchronously or incommensurately and results in a wide spectrum as exemplified in FIG. 16. The original spectrum may include enough components so that when the signal is regenerated it substantially accurately reflects the original signal. However, when the compression techniques according to the present invention are employed necessary information is lost thereby causing the regenerated signal to pull in from the original and become distorted as discussed supra and as shown in FIG. 17.

In order to eliminate the above-mentioned problems a unique windowing methodology according to the present invention is provided. In its essence, this windowing methodology is accomplished by applying a windowing function to the data set before compression thereby improving the level and accuracy of the compression method according to the present invention.

Figure 26:
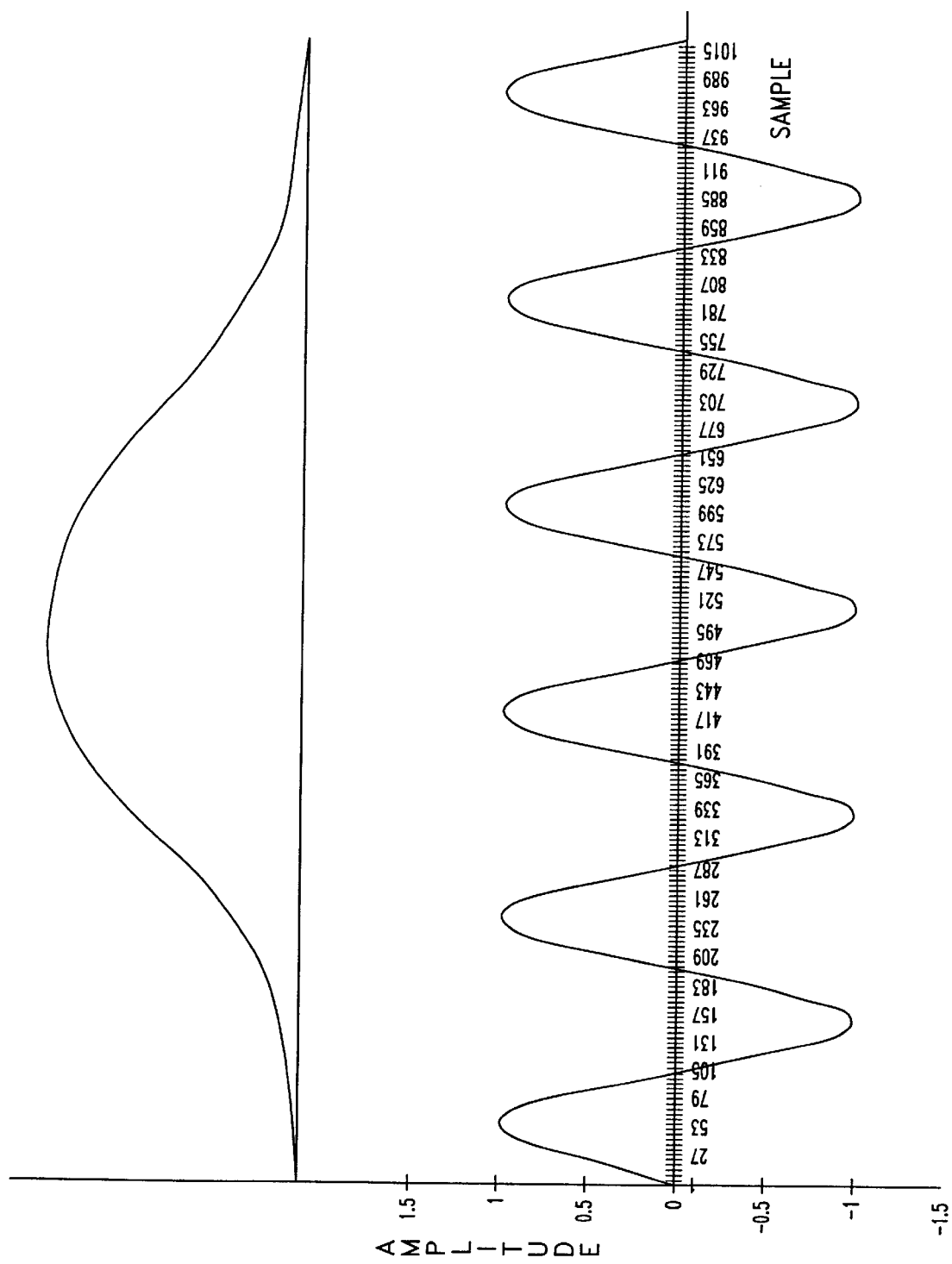
FIG. 26 is a graphical illustration of a windowing function and an incommensurate waveform.

Referring to FIG. 26, a windowing function 102 such as a Blackman window is multiplied by the sensed waveform or function 104 and then processed via the FFT. The result of this multiplication is that it zeros the ends of the sensed function so there is not a sharp discontinuity at the ends of the function. Accordingly, the ends of the spectrum have a lot less influence on the reconstructive waveform. Now, when an inverse FFT is preformed there must also be an inverse window to regenerate the original waveform. Inverse windowing is accomplished by multiplying the time base waveform by the inverse of the originally widow. This method forces the errors out to the ends of the waveform that causes the error at the ends of the waveform to worsen while increasing the accuracy at an intermediate portion between the ends. Thus, when the original waveform is regenerated the inconsistencies are forced out to the ends or edges of the regenerated original waveform and can then be truncated for obtaining an accurate representation of the intermediate part of the originally sensed waveform. Thus, the present invention obtains improved representation and improved compression by using fewer elements.

Figure 27:
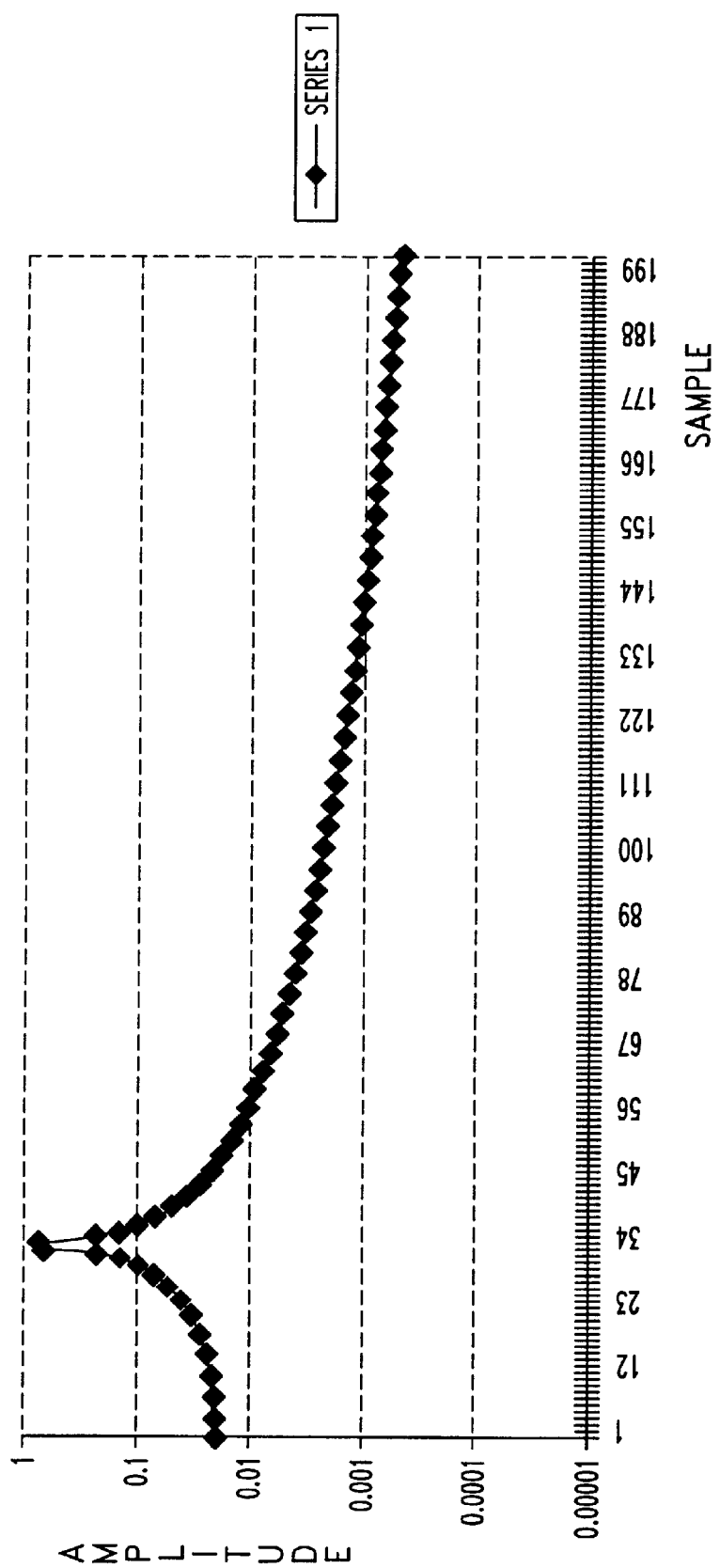
FIG. 27 is a graphical illustration of a spectrum plot of an incommensurate sampling of an example waveform having a frequency of 2032.25 Hertz.
Figure 28:
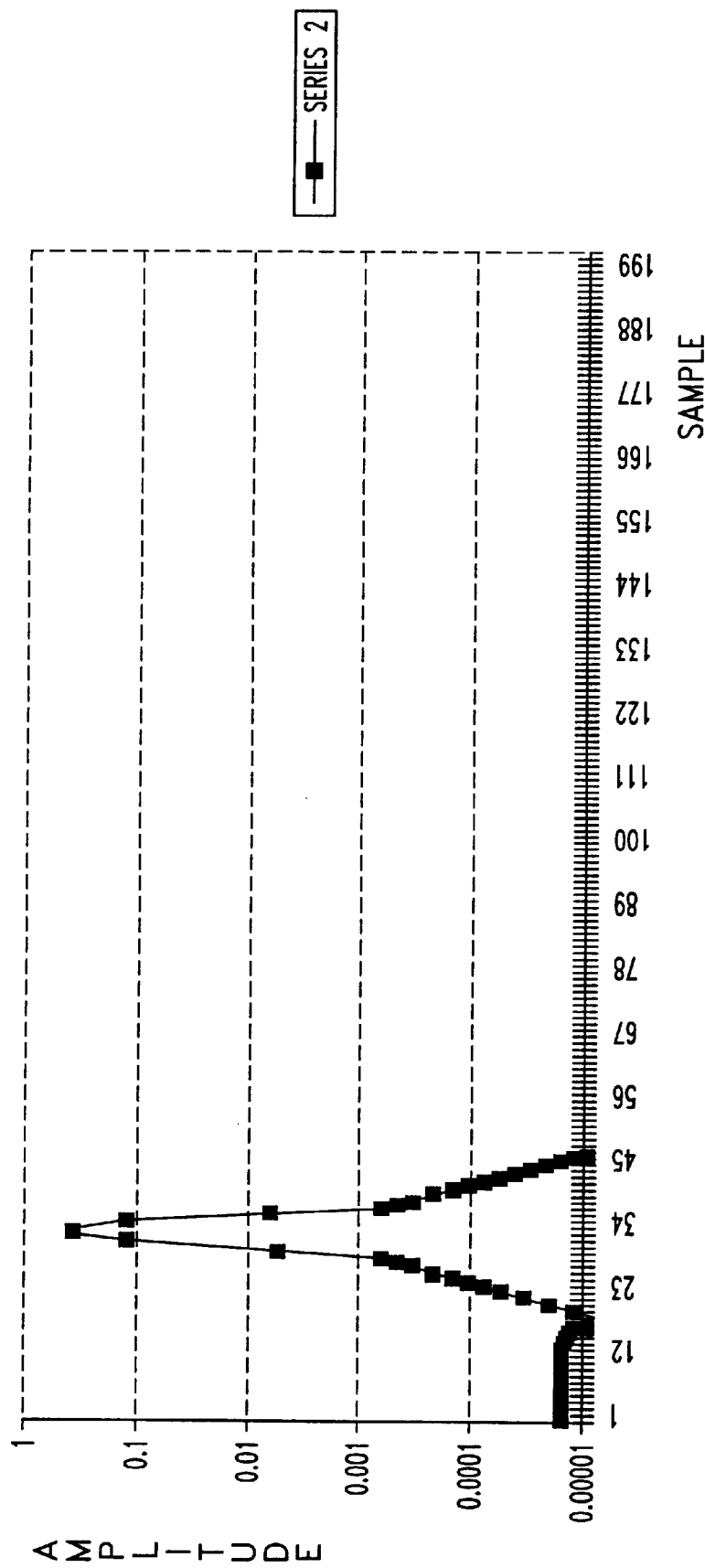
FIG. 28 is a graphical illustration of a spectrum plot of a commensurate sampling of an example waveform having a frequency of 2032.25 Hertz.

More specifically, and referring to FIG. 27, many spectral elements or components are required to accurately represent an incommensurate waveform due to the effects on the FFT process by incommensurate waveform. Thus, if a windowing function is applied to an incommensurate waveform before executing the FFT the resulting data has fewer significant spectral elements or components as shown in FIG. 28. This occurs because the end points of the data set or waveform are forced to zero. This naturally distorts the waveform, but since the windowing function is known, it can be corrected for when recreating the waveform.

The following steps outline one method according to the present invention for providing the windowing method for asynchronous sampling for improving data compression according to the present invention.

1. Collect a set of raw dynamic data,
2. Apply the windowing function to the data set,
3. Execute a FFT on the data set,
4. Compress the data set according to one or more of the compression methods of the present invention,
5. Transmit and/or store the data Then to retrieve the data:
6. Zero fill the data
7. Execute an inverse FFT on the data set,
8. Execute an inverse window on the data set, truncate according to the overlap method if desired, and
9. Display the data set.

Figure 29:
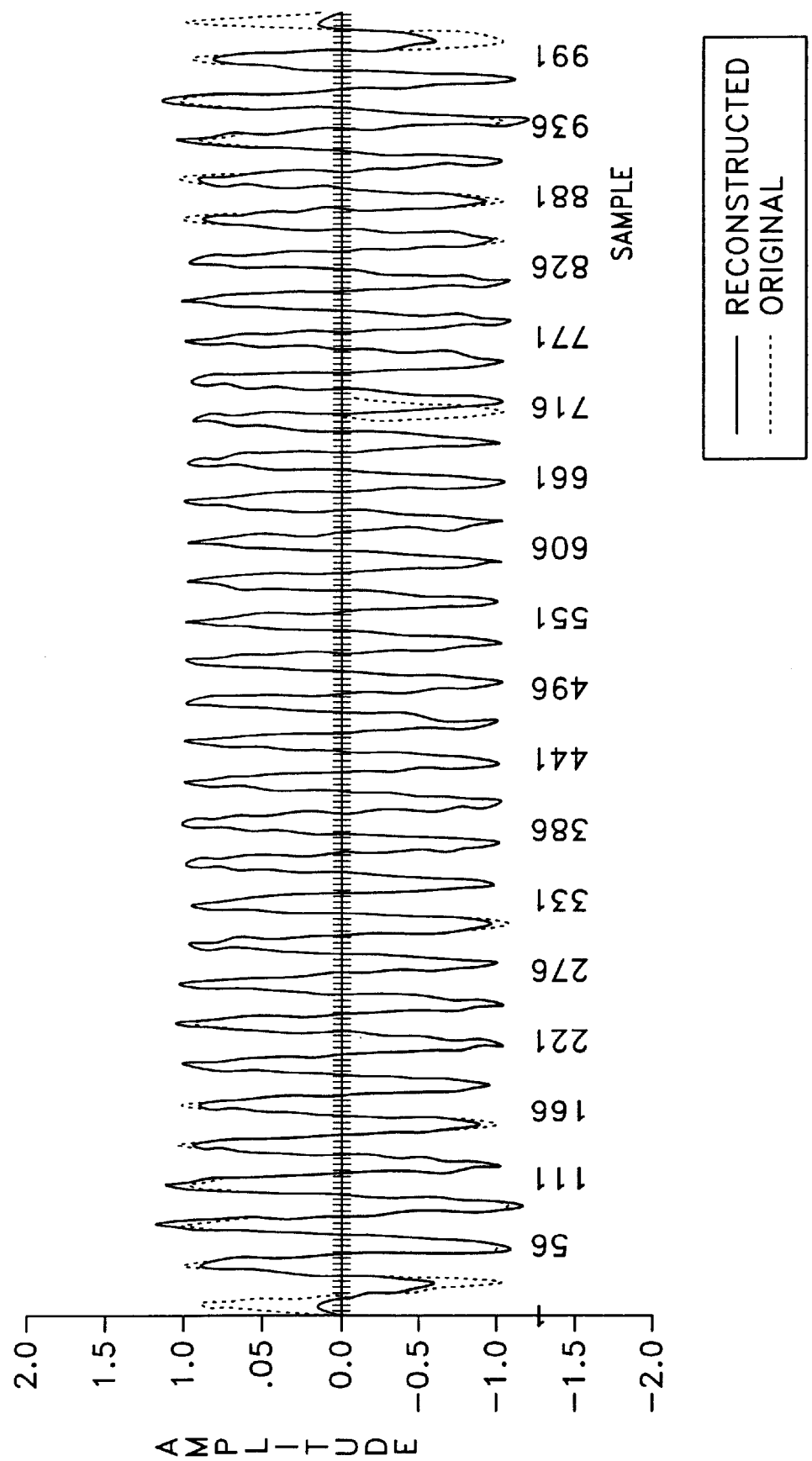
FIG. 29 is a graphical illustration of an example waveform having a frequency of 2032.25 Hertz and its reconstruction.
Figure 30:
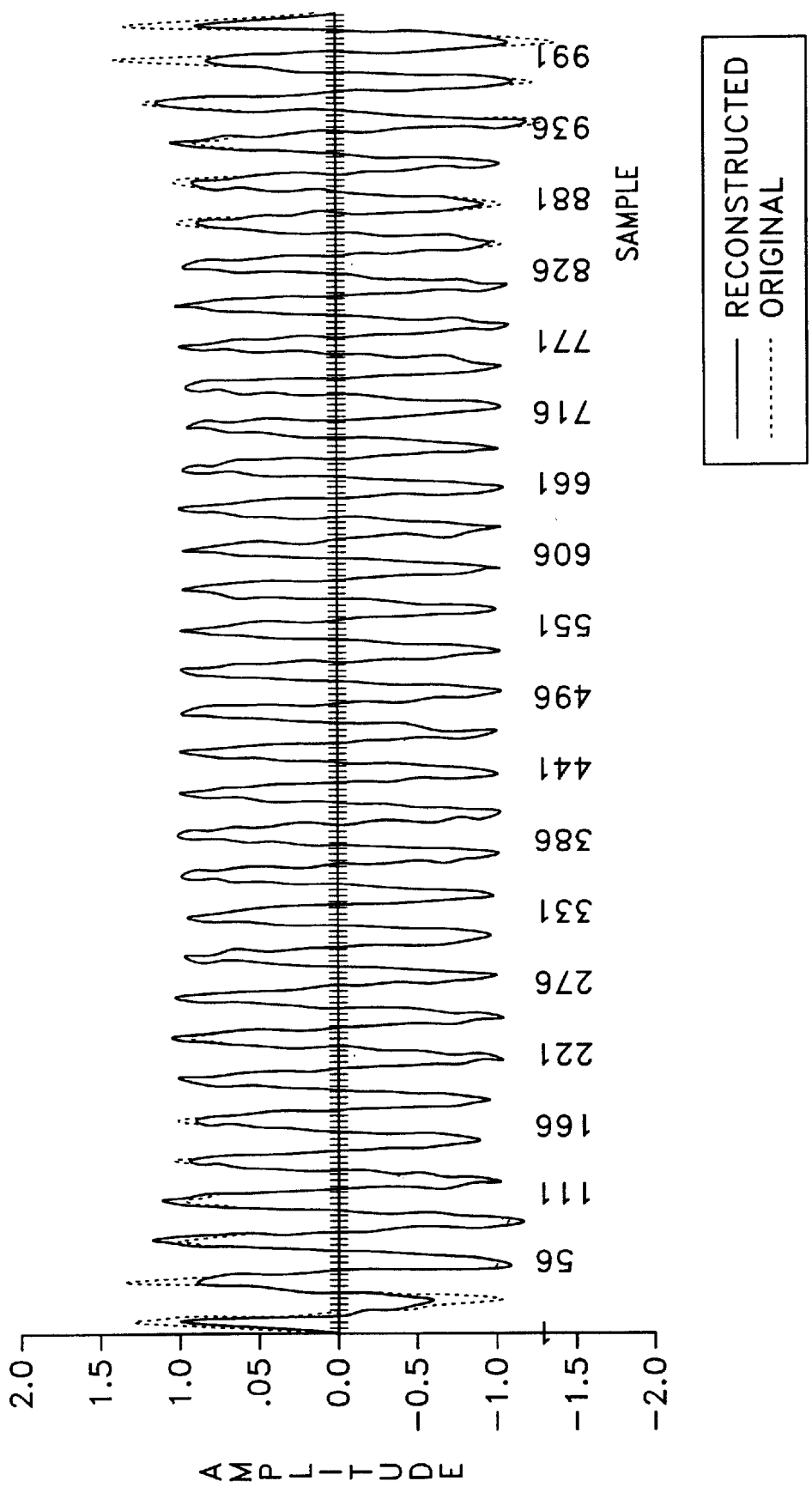
FIG. 30 is a graphical illustration of the example waveform having a frequency of 2032.25 Hertz and its reconstruction after a Blackman window was applied to the example waveform.

The following example shows the results of the windowing method according to the present invention. The signal used for the example is a 2032.25-Hertz signal or waveform that is sampled at 64 KHz. This places the sample frequency directly between two bins and creates an incommensurate waveform. The FFT plots shown in FIGS. 27 and 28 are of this signal. The plot in FIG. 29 shows both an original waveform 110 and a reconstructed waveform 112. The original waveform 110 was compressed using the criteria based compression method and the reconstructed waveform 112 was reconstructed using thirteen compressed spectral elements or components. The plot in FIG. 30 is of the same waveform, but now a Blackman window has been applied. Only six components resulted from the criteria based compression method and were used for reconstructing waveform 114.

Figure 31:
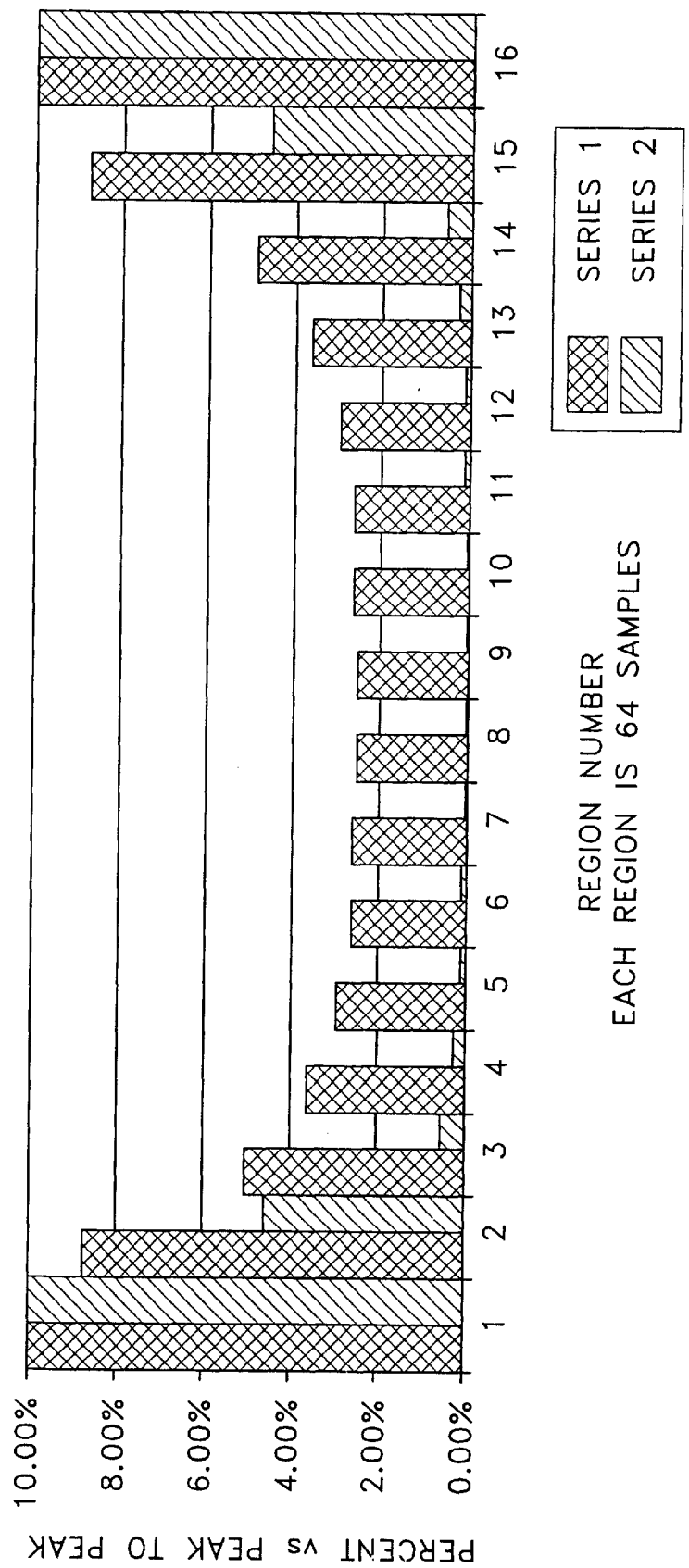
FIG. 31 is a plot or the maximum error over regions of the reconstructed waveforms shown in FIGS. 29 and 30.

FIG. 31 is a plot of the maximum error over a region of the waveform. Series 1 is the non-windowed spectral compression according to the criteria method of the instant invention and Series 2 is the windowed spectral compression according to the criteria method of the instant invention. The errors in the window method are localized to the edges of the waveform and can be removed by discarding these samples and only displaying regions 3 to 14.

A plot of error on a sample-by-sample basis once again revealed that the error resides on the outer extremes of the reconstructed waveform. In addition, the effects on a complex waveform composed of both incommensurate and commensurate spectral components revealed that an non-windowed spectral compression used more components that that of a windowed spectral compression and returns a more accurate representation of the original waveform. Hence, it has been shown that the windowing methodology according to the present invention provides both higher accuracy and better compression for incommensurate waveforms.

Notwithstanding, This method could be compared with the above-delineated methods using error analysis for determining the best method for the particular situation at hand.

Overlapping Data Sets

Figure 32:
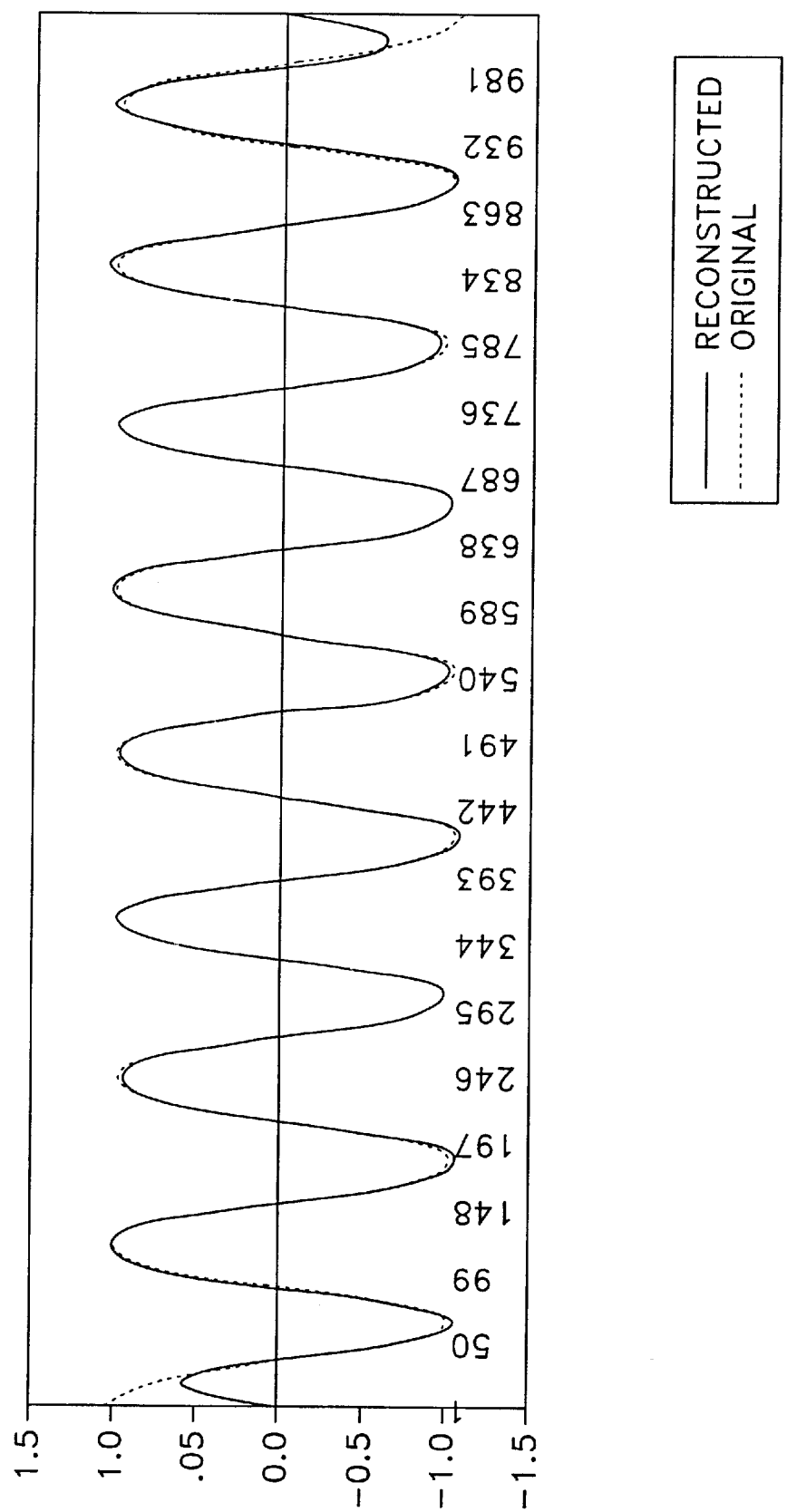
FIG. 32 is a graphical illustration of an original and a reconstructed waveform according to the present invention.

In its essence, and as described supra, one spectral compression method according to present invention takes a waveform and describes it in the frequency domain. Then the top peak frequencies are transmitted or stored to represent the waveform. This method works extremely well for frequency components that are synchronous with sampling rate. Unfortunately when there are frequency components that are asynchronous the reconstructed waveform can have significant error. Most of this error is at its extremes on the outer edges of the waveform as shown in FIG. 32. Waveform 120 is an original waveform and waveform 122 is a waveform reconstructed using the top thirteen components of the FFT processed waveform 120. Even if the number of components is increased to sixty-four there is still significant error at the edges of the waveform.

Figure 33:
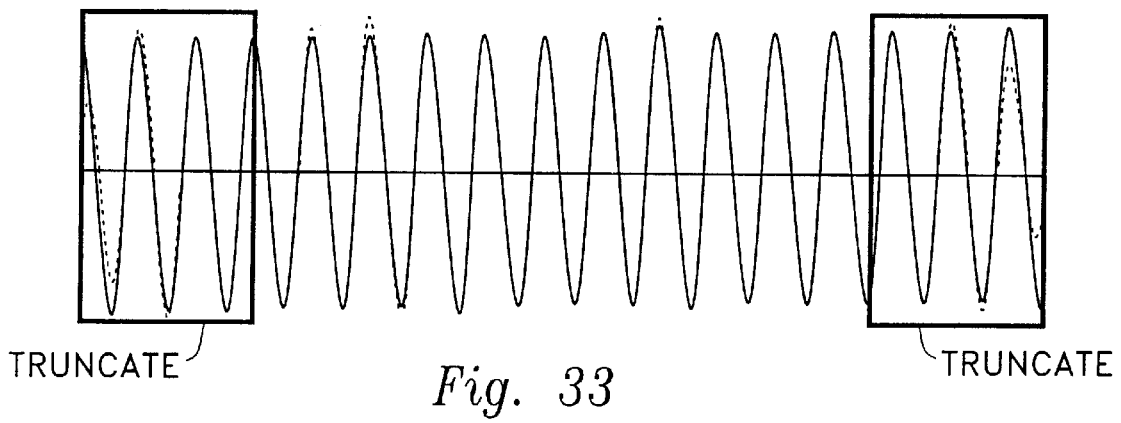
FIG. 33 is a graphical illustration of the reconstructed waveform shown in FIG. 32 with the ends truncated.

Referring to FIG. 33, one method for dealing with this problem according to the present invention is to sample over a longer period of time and throwing away or truncating the outer samples 124 and 126 after reconstructing the waveform via an inverse FFT.

Figure 34:
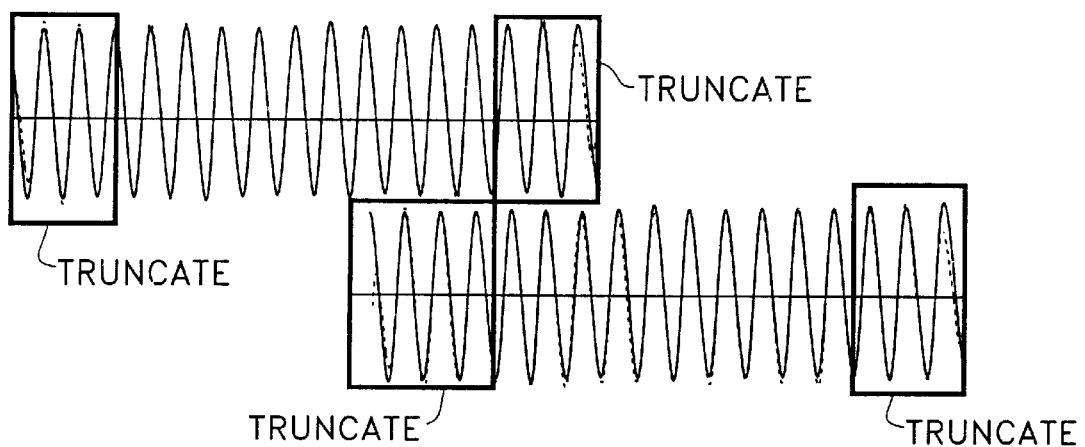
FIG. 34 is a graphical illustration of waveform overlapping according to the present invention.
Figure 35:
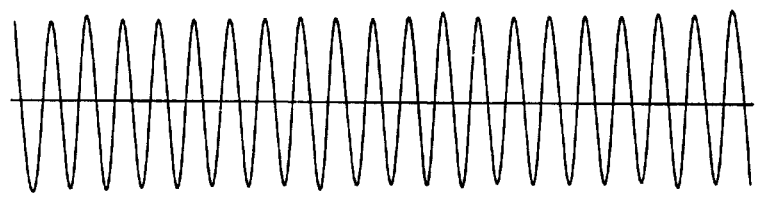
FIG. 35 is a graphical illustration of a composite waveform after waveform overlapping according to the present invention.

For example, instead of using 1024 samples and 32 shaft revolutions use 2048 samples and 64 revolutions, but use only the center 32 revolutions of data and discard the first and last 16 revolutions. Then, overlap the data from one waveform set having one interval to another waveform set having a different interval as shown in FIG. 34 to obtain a continuous composite waveform as shown in FIG. 35.

This unique overlapping method can be utilized to overcome the errors that are forced out to the ends of the waveforms resulting from the above delineated windowing method. Thus, when using the windowing method along with the overlapping method the ends of the waveforms including the errors are truncated. This results in eliminating the spectral elements due to error and thus provides fewer spectrum elements for compression.

By over lapping data sets the edges of each data set can be removed after uncompressing the data. This removes most of the error from the reconstructed data set.

This unique overlapping method can be combined with the use of the widowing method to improve representation using spectral compression according to the present invention. This technique allows a incommensurate waveform to be segmented and compressed for timely and efficient transmission but reconstructed without the distortion of the segmentations.

Spike Filter

In machine monitoring there are anomalies in material forming the shaft and as the shaft rotates these anomalies create spikes in the sensed vibration waveform that have nothing to do with the vibration of the shaft. Thus, when a Fast Fourier Transform is preformed on that waveform the spike shows up as a low level (same height) spread of spectrum elements across the entire sampled period. Thus, by using the above-delineated criteria method of collecting spectrum elements that are above a certain criteria level the spikes are filtered. In other words, by raising the floor of the spectrum or chopping the spectrum above a certain criteria level a new type of filter is created which is not a high pass, low pass or band pass filter but rather a spike rejection filter. Thus, the techniques according to present invention generate a new filter type.

Predetermined Sampling Number Method

Prior to sampling, the number of samples taken per revolution (the sample rate) is set to sample a period of collected data at a predetermined number of samples for the present shaft revolution and sampling is triggered to start at one occurrence of the mechanical reference mark and triggered to stop at the next occurrence of the sensing of the mechanical reference mark. Thus, if the shaft speeds up or slows down during the present shaft revolution the reference mark is sensed to soon or to late thereby resulting in the number of samples taken being either less than or greater than the predetermined number. One embodiment of the present invention overcomes this problem by always taken a specific predetermined number of samples per shaft revolution by either stopping the sampling when the specified predetermined number of samples is obtained without the subsequent sensing of the mechanical reference mark or by repeating a number of the last samples taken when the next occurrence of the sensing of the mechanical reference mark is sensed too soon.

In use and in operation, the system 10 is operatively coupled to at least one sensor 22 and as shown in FIG. 1, the system is operatively coupled to orthogonally disposed sensors 21 and 22 which in turn are removable or rigidly coupled to the machine 20 for sensing raw dynamic machine vibration signals correlative to machine status. The sensor 22 and/or 21 may take the form of, inter alia, a displacement (proximity) transducer, a velocity transducer and/or an acceleration transducer. In addition, the system 10 is preferably coupled to at least one timing transducer 24 for collecting a timing pulse correlative to, for example, a once per shaft revolution. The timing sensor 24 may take the form of, inter alia, a proximity probe which observes a physical gap change event, an optical pick up which observes a change in wave reflectivity event or a magnetic pick up.

The system 10 collects the raw vibration signals on a continuous basis from at least the one vibration sensor 22 and transmits the vibration signals to the sampling means 30 for sampling the vibration signals into discrete samples. Simultaneously, the system 10 collects a timing pulse from the timing sensor 24 for providing a measurement of shaft rotative speed and a reference point for measuring phase angle for relating a mechanical angle of the rotating shaft to the vibration signals of at least the one vibration sensor 22. In one preferred embodiment the timing sensor 24 transmits the timing pulse to the sampling control means 44. The sampling control means 44 incorporates the timing pulse into commands which are issued to the sampling means 30 to sample the vibration signals into discrete phase increments. Furthermore, the sampling control means 44, under the control of the processor 42, can issue commands to the sampling means 30 to sample the vibration signals at different sampling rates, sample modes based on elapsed time and/or change in machine speed or frequency span or mechanical phase wherein the data representation can be optimized to identify machine behavior under specific conditions.

The discrete samples from the sampling means 30 are transmitted to the processor 42 via the communication link 48 interposed between and operatively coupled to the sampling means 30 and the processor 42. Simultaneously, the sampling means 30 continues to collect, sample and transfer data from the vibration sensor 22 to the processor 42. Simultaneously, the processor 42 performs a fast fourier transform analysis on the incoming data to transform the data into spectral elements.

Figure 5:
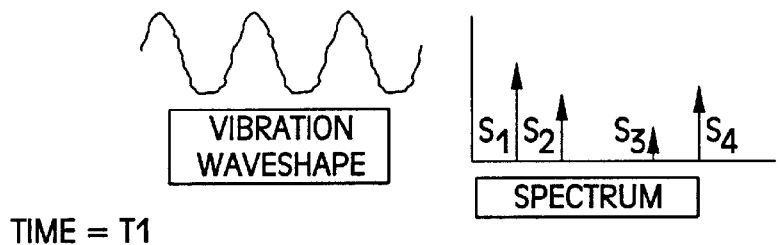
FIGS. 5 through 8 are graphical representations of continuous measurement data and graphical representations of spectrum elements resulting from the transformation of the continuous measurement data.

For example, and referring to FIG. 5, at time T1 a continuous vibration signal is sampled into a first data set of digital values and then transmitted to the processor 42 and transformed into a first series of spectral elements including both amplitude and phase information. The spectral elements are compared to a dominate criteria and those which pass this criteria are stored in the memory means 48 along with a unique identifying tag. FIG. 5 graphically shows that four spectral elements which have passed the dominant criteria and are tagged with a unique identifying tag including an element number and a real time value identifying a time in history when the corresponding instantaneous value of the vibration signal was captured by the vibration sensor 22. These spectral elements, $S_1$ through $S_4$, can then be transmitted to and stored in the host computer 60 along with at least one unique identifying tag associating an element number and a real time value to each transmitted spectral element.

Figure 6:
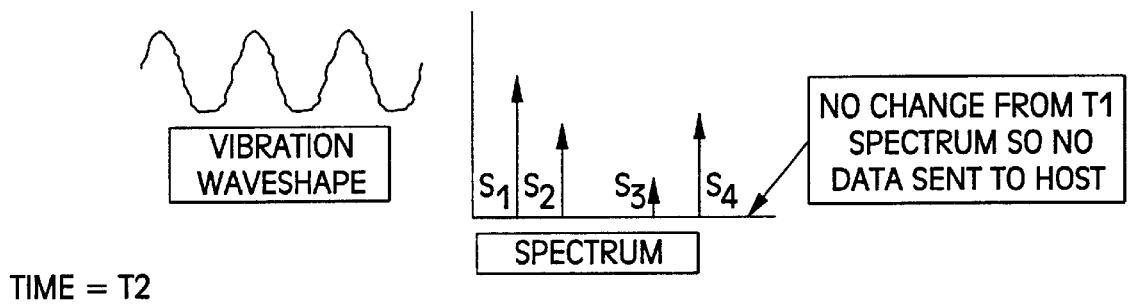

Referring to FIG. 6, at T2 a subsequent continuous vibration signal is sampled into a subsequent set of digital values which are transmitted to the processor 42 and transformed into a subsequent series of spectral elements including both amplitude and phase information. The subsequent series of spectral elements are also compared to the dominant criteria and those which pass are stored in the memory means 48 and compared to the first or previous set of spectral elements which have been previously stored in the memory means for determining any anomalous behavior between the two. Referring to FIG. 6, there is no change in the spectral elements from T1. Therefore the data is preferably not saved in memory means 48 nor is it sent to the host computer 60.

Figure 7:
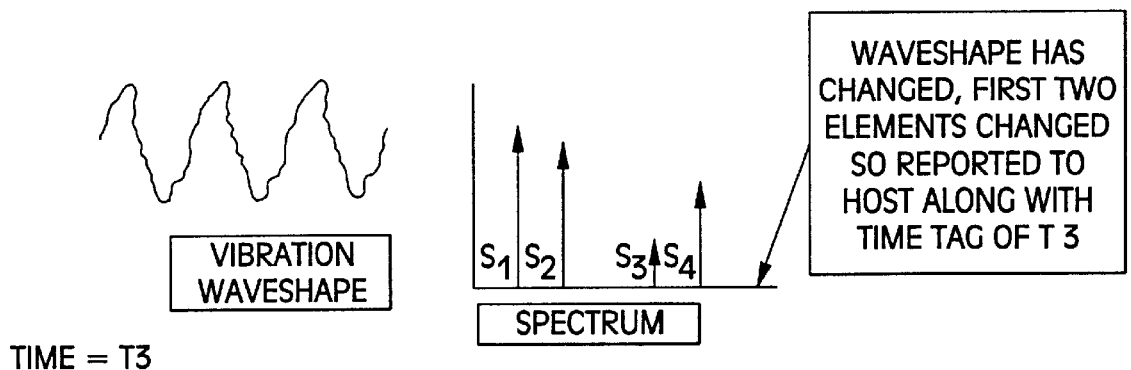

Referring to FIG. 7, at time T3 the vibration waveshape captured from the transducer includes anomalies. Thus, the waveshape has changed and referring to the spectrum plot it can be noted that the first two elements, S1 and S2, are anomalous and thus are stored in memory means 48 and reported to the host computer 60 along with the time tag of T3.

Figure 8:
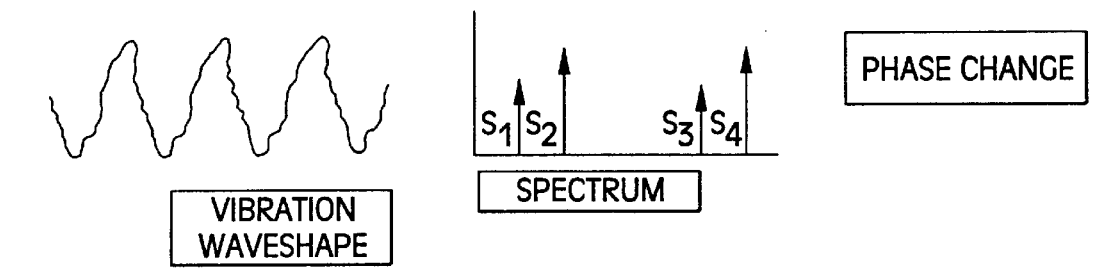

Referring to FIG. 8, at time T4 a phase change of the vibration waveshape has occurred and thus results in two anomalous elements $S_1$ and $S_2$ when compared to the previous set of spectral elements shown in FIG. 7. Thus, the first two elements, $S_1$ and $S_2$, shown in FIG. 8 are stored in memory means 48 and reported to the host computer 60 along with the time tag of T4.

The host computer 60 can recreate a continuous vibration signal at any given time by using the anomalous spectral elements for that time and sequencing backward through the stored spectral element sets to capture and use only those elements which have different element numbers than the anomalous spectral elements and which are needed to form the original dominant spectral content. For example, the computer can re-create the continuous vibration signal shown in FIG. 7 by first sequestering the anomalous spectral elements S1 and $S_2$ shown in FIG. 7 and then sequencing backward and sequestering spectral elements $S_3$ and $S_4$ from the previously stored spectral elements found in the host computer 60. Once the computer has sequestered a given number of spectral elements contained in the original dominant spectral content it may perform an inverse fourier transform analysis to recreate the continuous vibration signal for the given time in history.

Figure 10:
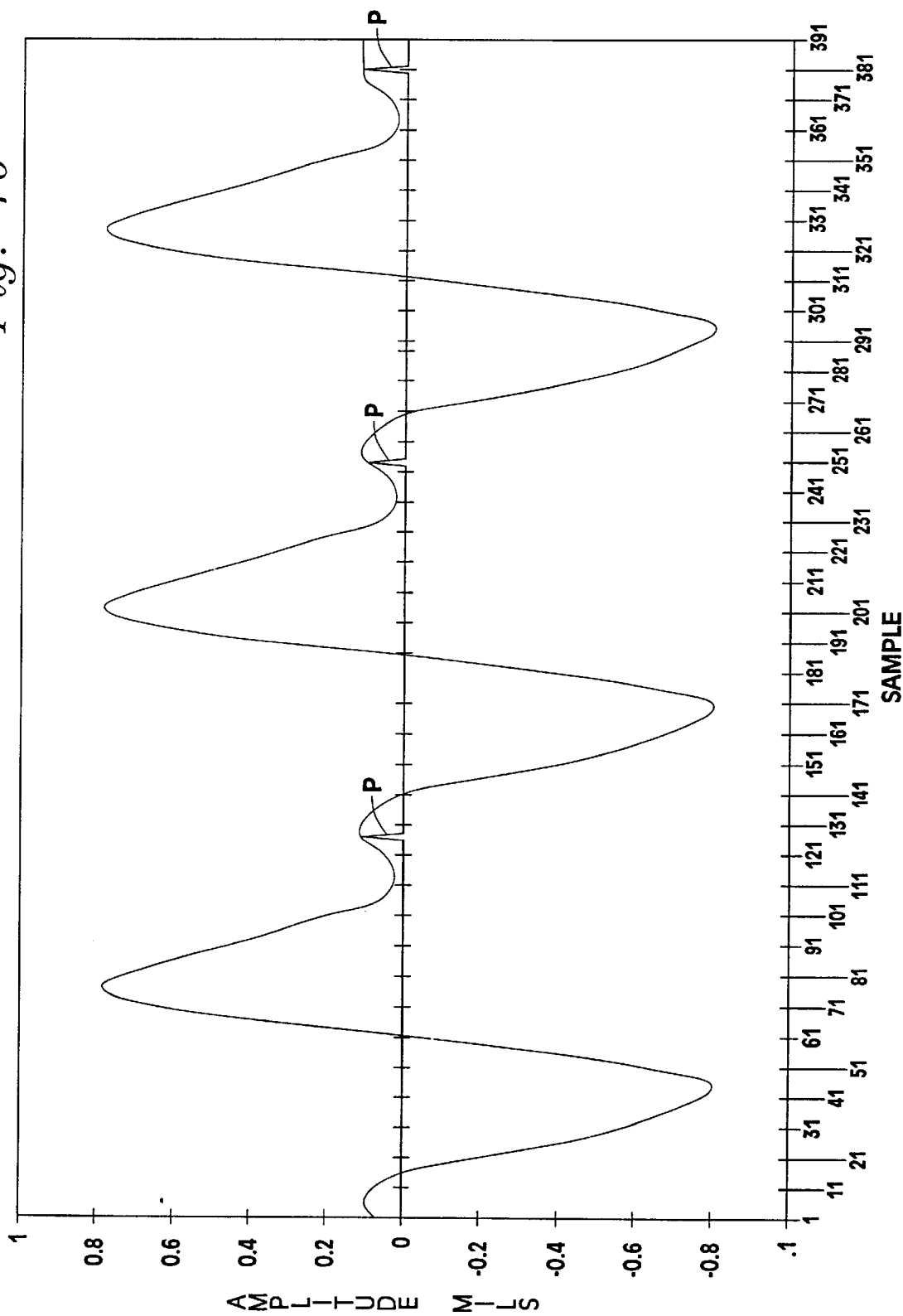
FIG. 10 is a graphical representation of the mechanical phase reference marks and continuous vibration signals reconstructed from the continuous vibration signals shown in FIG. 9 after being compressed according to the present invention.
Figure 11:
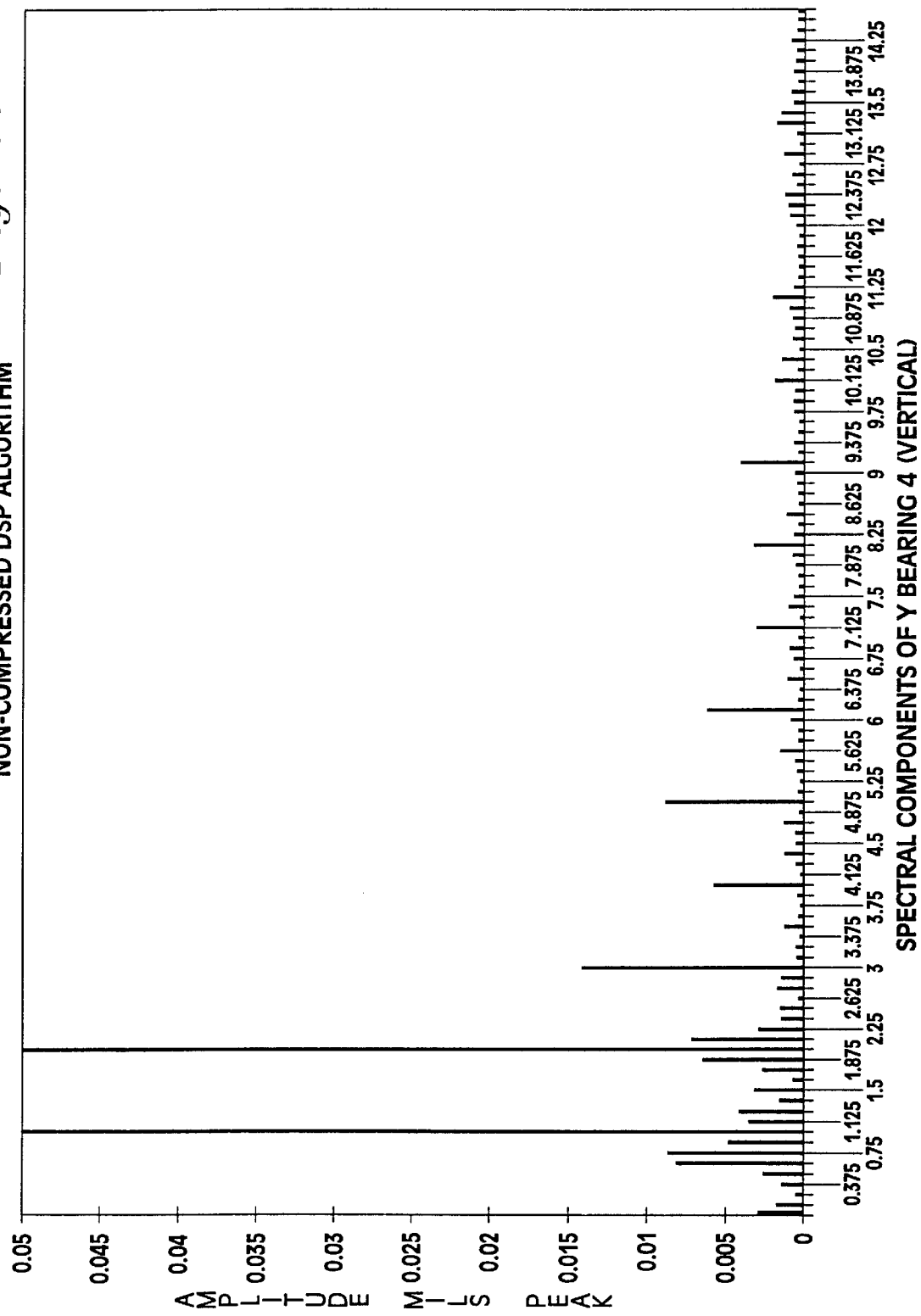
FIGS. 11 and 12 respectively show uncompressed and compressed spectrum plots of the signals S and S' respectively shown in FIGS. 9 and 10.
Figure 12:
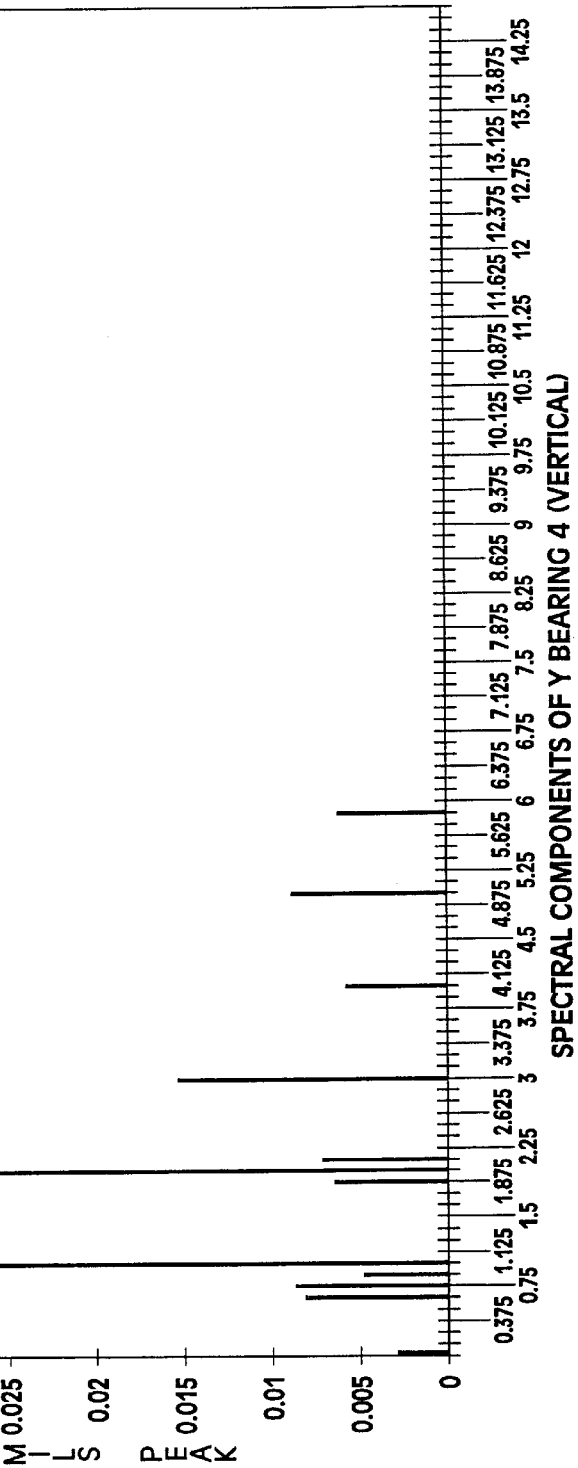

FIGS. 11 and 12 respectively show uncompressed and compressed spectrum plots of the signals S and S' respectively shown in FIGS. 9 and 10. The compressed plot results from using the criteria of a fixed quantity of largest elements according to the invention. Specifically, FIG. 12 results in using twelve of the largest elements.

It will be appreciated that the machine data can be directly communicated from the sensors 21, 22, 24 to the remote computer 60 in order to perform the functions performed by the sampling means 30 and the computational means 40.

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. A method for compressing measurement data correlative to status of operation of a machine, the steps including:
   monitoring a plurality of rotations of a rotating shaft of the machine;
   determining a period of each of said plurality of rotations defining previous periods;
   predicting a subsequent period of rotation of the rotating shaft as a function of said previous periods;
   sensing machine data correlative to the status of operation of the machine;
   sampling said sensed machine data at a sampling rate that is a function of said subsequent period;
   transforming said sampled data into spectral elements;
   comparing said spectral elements to a user definable criteria for retention; and
   compressing said sampled data by storing in a memory means those spectral elements which have passed said user definable criteria for retention wherein said stored spectral elements are correlative to the status of operation of the machine.

2. A signal processing method for processing machinery signals correlative to status of operation of a machine, the steps including:
   (a) monitoring periods of rotation of a rotating shaft of the machine;
   (b) determining a last period of rotation of the rotating shaft from the monitored periods for defining a determined period;
   (c) dividing the determined period into an integer number of smaller periods, one said smaller period defining a sampling period;
   (d) sensing a signal correlative to the status of operation of the machine during a next period of rotation of the rotating shaft subsequent to said last period;
   (e) sampling said sensed signal at a sampling rate that is a function of said sampling period, and
   (f) storing said sampled sensed signal for obtaining data correlative to the status of operation of the machine.

3. The method of claim 2 further including the step of iteratively repeating steps (b) through (f) for an integer number of successive periods of rotation of the rotating shaft of the machine.

4. A signal processing method for processing machinery signals correlative to status of operation of a machine, the steps including:
   (a) monitoring periods of rotation of a rotating shaft of the machine;
   (b) determining a last period of rotation of the rotating shaft from the monitored periods for defining a first period;
   (c) determining a previous period of rotation of the rotating shaft from the monitored periods that is immediately prior to said last period for defining a second period;
   (d) predicting a next period of rotation of the rotating shaft subsequent to said last period as a function of both said first period and said second period for defining a predicted period of rotation of the rotating shaft;
   (e) sensing a signal correlative to status of operation of the machine during said predicted next period;
   (f) sampling said sensed signal at a sampling rate that is a function of said predicted next period, and
   (g) processing said sampled sensed signal for obtaining data correlative to the status of operation of the machine.

5. The method of claim 4 wherein said step of predicting said next period of rotation of the rotating shaft subsequent to said last period as a function of both said first period and said second period for defining said predicted period includes the step of adding said first period to the difference between said first period and said second period for defining said predicted period of rotation of the rotating shaft.

6. The method of claim 5 wherein said step of sampling said sensed signal at said sampling rate that is the function of said predicted next period includes the step of sampling said sensed signal at a sampling rate that is a quotient resulting from a division of said predicted next period by a synchronous sampling rate.

7. The method of claim 6 wherein said step of sampling said sensed signal at said sampling rate that is said quotient resulting from said division of said predicted next period by said synchronous sampling rate includes the step of defining said synchronous sampling rate as a multiple of the rotating shaft speed.

8. The method of claim 4 further including the step of iteratively repeating steps (b) through (g) for an integer number of successive periods of rotation of the rotating shaft of the machine.

9. A method for compressing measurement data correlative to status of operation of a machine, the steps including:
   determining a speed of a rotating shaft of a machine during each shaft revolution;
   determining a sampling period as a function of the determined rotating shaft speed;
   sensing machine data correlative to the status of operation of the machine;
   sampling said sensed data at a sampling rate that is a function of said sampling period determined as the function of the determined rotating shaft speed;
   transforming said sampled data into spectral elements;
   comparing said spectral elements to a user definable criteria for retention; and
   compressing said sampled data by storing in a memory means those spectral elements which have passed said user definable criteria for retention wherein said stored spectral elements are correlative to the status of operation of the machine.

10. A method for compressing measurement data correlative to status of operation of a machine, the steps including:
   sensing a series of sets of machine data correlative to the status of operation of the machine;
   sampling the series of sets of machine data;
   applying a windowing function to the sampled series of sets of machine data;
   transforming the windowed sampled series of sets of machine data into first intervals of spectral elements;
   truncating at least one end of each of the first intervals of spectral elements;
   transforming the windowed sampled series of sets of machine data into second intervals of spectral elements wherein the second intervals overlap the first intervals;
   truncating at least one end of each of the second intervals of spectral elements;
   comparing both the first and second intervals of spectral elements, absent the truncated ends, to a user definable criteria for retention; and
   compressing the windowed sampled series of sets of machine data by storing in a memory means those spectral elements which have passed the user definable criteria for retention wherein the stored spectral elements are correlative to the status of operation of the machine.

\* \* \* \* \*